US010338017B2

(12) United States Patent
Sonderegger et al.

(10) Patent No.: US 10,338,017 B2
(45) Date of Patent: Jul. 2, 2019

(54) ELECTRIC GRID HIGH IMPEDANCE CONDITION DETECTION

(71) Applicant: Itron, Inc., Liberty Lake, WA (US)

(72) Inventors: Robert Sonderegger, Oakland, CA (US); Timothy James Driscoll, Raleigh, NC (US)

(73) Assignee: Itron, Inc., Liberty Lake, WA (US)

( * ) Notice: Subject to any disclaimer, the term of this patent is extended or adjusted under 35 U.S.C. 154(b) by 525 days.

(21) Appl. No.: 14/702,759

(22) Filed: May 4, 2015

(65) Prior Publication Data
US 2016/0327603 A1 Nov. 10, 2016

(51) Int. Cl.
| G01N 27/02 | (2006.01) |
| G01R 19/25 | (2006.01) |
| G06Q 50/06 | (2012.01) |
| G01R 27/16 | (2006.01) |
| G01R 31/08 | (2006.01) |
| G06Q 10/06 | (2012.01) |
| G01R 22/06 | (2006.01) |
| G01R 27/08 | (2006.01) |
| H02J 3/00 | (2006.01) |

(52) U.S. Cl.
CPC ......... *G01N 27/02* (2013.01); *G01R 19/2513* (2013.01); *G01R 27/16* (2013.01); *G01R 31/086* (2013.01); *G06Q 10/06* (2013.01); *G06Q 50/06* (2013.01); *G01R 22/066* (2013.01); *G01R 27/08* (2013.01); *H02J 3/00* (2013.01); *H02J 2003/007* (2013.01); *Y02E 60/74* (2013.01); *Y02E 60/76* (2013.01); *Y04S 10/30* (2013.01); *Y04S 10/522* (2013.01); *Y04S 40/22* (2013.01)

(58) Field of Classification Search
CPC .... G01N 27/02; G01R 19/2513; G01R 27/16; G01R 31/086; G01R 11/24; G01R 19/165; G01R 22/06; G01R 31/02; G01R 31/026; G06Q 10/06; G06Q 50/06; H02J 2003/007; H02J 3/00; Y02E 60/74; Y02E 60/76; Y04S 10/30; Y04S 10/522; Y04S 10/54
USPC ......................................................... 702/58
See application file for complete search history.

(56) References Cited

U.S. PATENT DOCUMENTS

| 7,714,592 B2 * | 5/2010 | Radtke ................... G01R 27/16 |
| | | 324/629 |
| 8,437,883 B2 | 5/2013 | Powell et al. |
| 8,577,510 B2 | 11/2013 | Powell et al. |
| 9,709,604 B2 * | 7/2017 | Driscoll ................... G01R 11/24 |
| 2003/0158677 A1 * | 8/2003 | Swarztrauber ......... G01D 4/008 |
| | | 702/62 |
| 2008/0109387 A1 * | 5/2008 | Deaver ............ G01R 19/16547 |
| | | 705/412 |
| 2009/0115427 A1 | 5/2009 | Radtke et al. |
| 2009/0289637 A1 * | 11/2009 | Radtke .................... G01R 27/16 |
| | | 324/629 |
| 2010/0271225 A1 * | 10/2010 | Palmer ................... G01R 31/026 |
| | | 340/650 |
| 2010/0324844 A1 * | 12/2010 | Marti ..................... H02H 3/385 |
| | | 702/61 |
| 2011/0153244 A1 | 6/2011 | Rocha Alves, Jr. et al. |
| 2012/0059609 A1 * | 3/2012 | Oh ........................ G01R 22/066 |
| | | 702/62 |
| 2012/0062210 A1 | 3/2012 | Veillette |
| 2013/0151026 A1 | 6/2013 | Hughes |
| 2013/0335061 A1 | 12/2013 | de Buda et al. |
| 2014/0032506 A1 | 1/2014 | Hoey et al. |
| 2014/0167528 A1 | 6/2014 | Lancaster |
| 2014/0300210 A1 | 10/2014 | Abi-Ackel et al. |
| 2014/0368189 A1 * | 12/2014 | Bernheim ............. G01R 22/066 |
| | | 324/115 |
| 2015/0241488 A1 * | 8/2015 | Sonderegger ........ G01R 22/066 |
| | | 702/65 |
| 2016/0320431 A1 | 11/2016 | Driscoll |
| 2017/0038415 A1 * | 2/2017 | Dasgupta ............. G01R 22/066 |
| 2017/0315153 A1 | 11/2017 | Driscoll |

FOREIGN PATENT DOCUMENTS

| EP | 2377217 | 10/2011 |
| WO | WO2009134832 | 11/2009 |

OTHER PUBLICATIONS

Office action for U.S. Appl. No. 14/702,756, dated Nov. 9, 2016, Driscoll et al., "Detection of Electrical Theft from a Transformer Secondary", 6 pages.
The PCT Search Report and Written Opinion dated Jul. 22, 2016 for PCT application No. PCT/US2016/030129, 12 pages.
PCT Search Report and Written Opinion dated Aug. 25, 2016 for PCT Application No. PCT/US16/30120, 12 Pages.
The Australian Office Action dated Nov. 7, 2017 for Australian patent application No. 2016258839, a counterpart foreign application of U.S. Pat. No. 9,709,604, 3 pages.
The Canadian Office Action dated Nov. 29, 2017 for Canadian Patent Application No. 2984679, a counterpart foreign application of U.S. Pat. No. 9,709,604, 4 pages.

(Continued)

*Primary Examiner* — Tan T. Nguyen
(74) *Attorney, Agent, or Firm* — Lee & Hayes, P.C.

(57) ABSTRACT

Techniques for detecting high impedance conditions in an electrical grid are described herein. In one example, impedance is calculated for each of a plurality of locations within the electrical grid, such as at electrical meters. The impedances may be calculated as a change in voltage divided by a change in current, such as between sequential voltage/current measurements. Statistics may be maintained, including the calculated impedances. In three examples, statistics may be used to identify growth in impedance over multiple days, to identify growth in impedance over multiple hours, and to identify a meter for which impedance is higher than impedance for other meters attached to a single transformer. In a further example, instances of impedance over a threshold value may be identified, from among the maintained statistics. The instances of high impedance may be reported for reasons including cost and safety.

21 Claims, 18 Drawing Sheets

(56) References Cited

OTHER PUBLICATIONS

A. J. Berrisford, "A tale of two transformers: An algorithm for estimating distribution secondary electric parameters using smart meter data", 26th IEEE Canadian Conference of Electrical and Computer Engineering (CCECE), May 2013, pp. 1-6.

The Australian Office Action dated Nov. 5, 2018 for Australian patent application No. 2016258844, a counterpart foreign application of U.S. Appl. No. 14/702,759, 3 pages.

The Canadian Office Action dated Oct. 5, 2018 for Canadian patent application No. 2984490, a counterpart foreign application of U.S. Appl. No. 14/702,759, 11 pages.

* cited by examiner

ELECTRIC GRID HIGH IMPEDANCE CONDITION DETECTION

RELATED APPLICATIONS

This patent application is related to U.S. patent application Ser. No. 14/702,756, titled "Detection of Electrical Theft from a Transformer Secondary," filed on 3 May 2015, commonly assigned herewith, and hereby incorporated by reference.

BACKGROUND

In an electrical utility grid, poor electrical conductivity may result from improper wire splicing, tapping, connections or cable aging. Such poor electrical conductivity results in high impedance. When current is drawn through a high impedance connection, there is a voltage drop across the connection and associated heating. Heat may further degrade the connection, causing the high impedance connection to become even more impeded. Deterioration of a high impedance connection can occur over a period of hours, days, weeks, months, or years, depending upon the nature and problems of the connection, and the magnitudes of the currents (loads). A high impedance connection can result in energy losses due to heating, and can result in voltage problems due to excess voltage drop across the connection. Both of these problems may worsen as the connection deteriorates.

Energy losses also result from theft. In one example, energy diversion results when an unmetered load is attached to the secondary of a transformer. Because the load is unmetered, normal billing procedures are not performed. In a second example, energy diversion results when a "rogue" or unauthorized transformer is attached to a primary power line, and unmetered loads are attached to that transformer's secondary.

Thus, energy losses may result from high impedance connections and from unmetered loads. Both result in financial losses to utility companies, and both may involve unsafe wiring conditions.

BRIEF DESCRIPTION OF THE DRAWINGS

The detailed description is described with reference to the accompanying figures. In the figures, the left-most digit(s) of a reference number identifies the figure in which the reference number first appears. The same numbers are used throughout the drawings to reference like features and components. Moreover, the figures are intended to illustrate general concepts, and not to indicate required and/or necessary elements.

DETAILED DESCRIPTION

Figure 1:
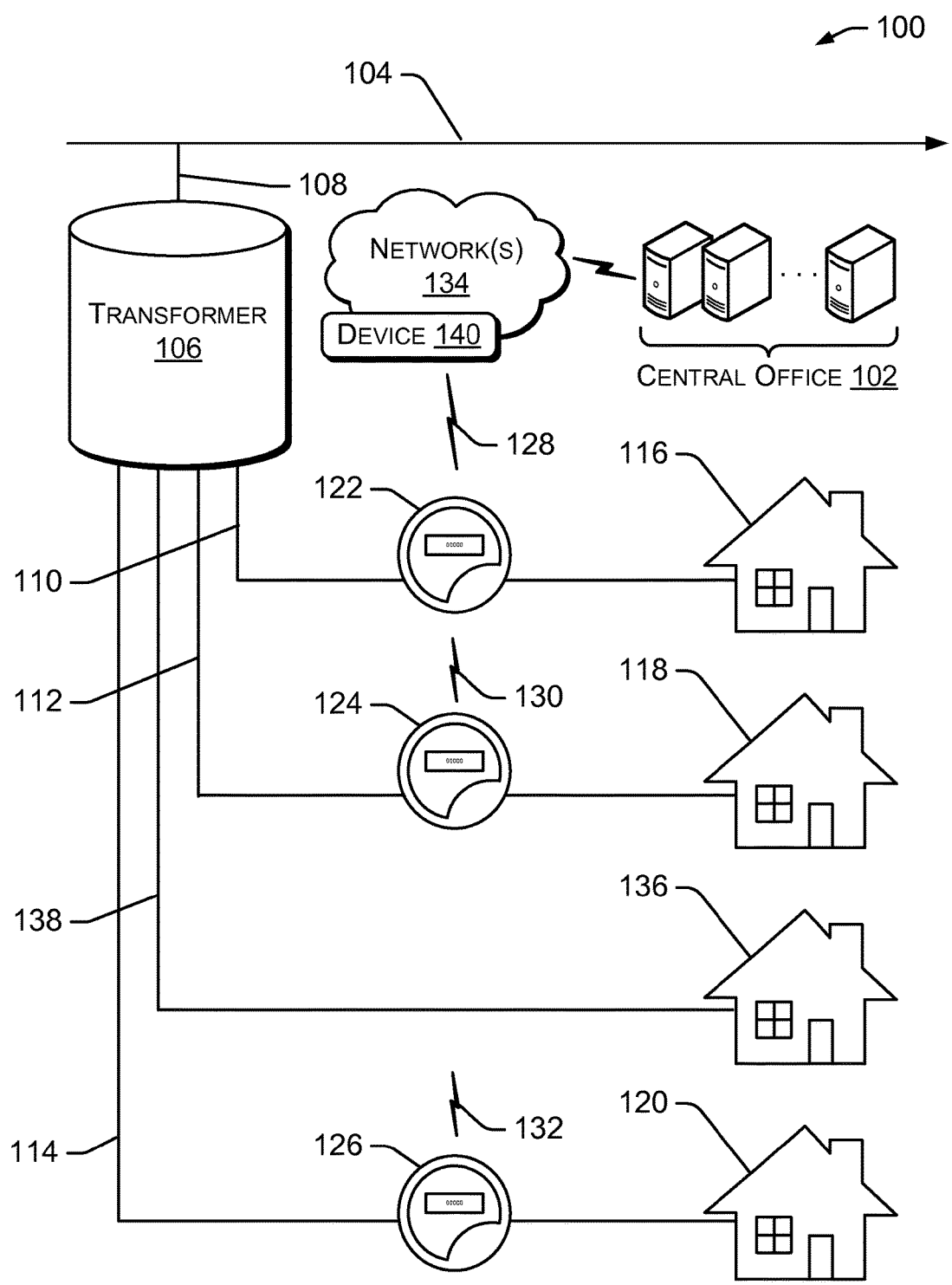
FIG. 1 is a block diagram of an example of a smart electrical grid, wherein smart meters and/or a central or back office are configured to calculate impedance seen by the meter and to thereby identify high impedance situations, and wherein smart meters and/or a central or back office are configured to calculate a voltage at the transformer secondary for use in identifying possible instances of power diversion.

Overview of Techniques to Detect High Impedance

The disclosure describes techniques for recognizing high impedance conditions in wiring and/or wiring connections. In one example, a plurality of electrical meters repeatedly calculate impedance at different locations, different times, and under different load conditions, within a smart electrical grid. The impedances may be calculated as change in measured voltage divided by change in measured current. Data representing the calculated impedances and/or the underlying paired voltage and current measurements may be maintained over time. The data may be evaluated statistically, according to different methods and using different techniques, to detect instances of high impedances at particular locations in the electrical grid. The statistics may identify slow growth in impedance over months and years, rapid growth in impedance over hours and days, or impedance at particular meter(s) that is significantly and/or statistically greater than impedance at other meters, such as other meters associated with a same transformer.

Overview of Techniques to Recognize Energy Diversion

The disclosure describes techniques for recognizing energy diversion (i.e., theft). In one example, a bad actor attaches an unmetered load to a secondary of a transformer. In another example, the bad actor attaches an unauthorized transformer to a primary supply line, and then attaches unmetered load(s) to that transformer.

The techniques for recognizing energy diversion may involve calculating a voltage at a secondary of each of a plurality of transformers. (Note that transformers typically do not have voltage measuring abilities.) The voltage may be calculated independently by each meter associated with the transformer, and the results of all such meters averaged. For each meter, entries in a time series of paired voltage and current measurements may be used to calculate an estimation of the impedance seen by the meter as change in voltage over change in current. The voltage at the transformer secondary may be calculated as the voltage measured at the meter, plus the product of the measured current and calculated impedance.

The calculated voltages at the secondary of multiple transformers may be compared to identify transformer(s) having a calculated voltage that is lower than an expected range or more variable than expected. In one example, several transformers may have a consistent voltage relationship hierarchy (e.g., a few transformers consistently a couple volts higher, and a few transformers consistently a couple volts lower). However, a transformer may be identified that frequently changes position within the voltage relationship hierarchy. The inconsistency of the identified transformer may be related to an unmetered load on its secondary winding.

However, load changes on the identified transformer may explain the volatility of the transformer's voltage. After such load changes are confirmed or denied by data obtained from meters associated with the transformer, it will be known if a report of power diversion is indicated.

Example System and Techniques

FIG. 1 shows an example of a smart electrical grid 100. In one aspect of the grid 100, smart meters and/or a central or back office are configured to calculate impedance at each of a plurality of meters and to thereby identify high impedance situations. In another aspect of the grid 100, voltages at a plurality of transformers may be calculated for transformers not having their own voltage meters. In this aspect, the smart meters and/or the back office are configured to calculate a voltage at each of a plurality of transformer secondary coils so that voltages at different transformers may be compared in the course of identifying possible instances of unmetered power diversion.

FIG. 1 shows portions of the smart electrical grid 100, including a central office 102 (sometimes called a back office, office, utility company headquarters, or similar). A primary feeder 104 is represented by an arrow directed away from a substation (not shown). The primary feeder 104 is connected to a transformer 106 by wiring 108. The transformer 106 provides power over low voltage lines 110, 112 and 114 to customers 116, 118 and 120. The power is metered by meters 122, 124 and 126. Each meter communicates with the central office 102, using radio frequency (RF), power line communications (PLC) or other technologies. In the example shown, RF signals 128, 130, 132 provide two-way communication through one or more networks 134 (such as the Internet) to the central office 102.

FIG. 1 shows that a building 136 is connected in by unauthorized wiring 138 to the transformer 106. The building may be a house, shop, greenhouse, garage, business, etc. By connecting directly to the secondary of the transformer 106, the building 136 diverts power and becomes an unmetered load on the electrical grid 100. However, as will be more fully developed in subsequent discussion, the meters 122, 124, 126 and/or central office 102 are configured to provide information indicating unmetered power consumed at building 136.

In the example smart grid 100, one or more devices 140, such as a concentrator, router or other device may be utilized by the smart grid to collect, transfer or otherwise process consumption data, software and/or other information in one or more locations between the meters 122-126 and office 102.

The smart grid 100 is configured to recognize instances of high impedance. Examples of high impedance include poor electrical connections, degraded wiring and other infrastructure problems. In one example, the meters 122-126 repeatedly make paired voltage and current measurements. The measurement data allows calculation of impedance at the meters over time. A number of techniques may be considered to determine instances of high impedance, and may be performed at each meter, at the central office, or in a distributed manner over two or more locations. In one example, a statistical growth in impedance over time may indicate a slowly deteriorating connection, wiring or other infrastructure. In another example, a sudden increase in impedance may be recognized and associated with a cable or connection breakdown. In a further example, impedance that is statistically higher than other meters on the same transformer's secondary may indicate a high impedance situation that was already present as the techniques discussed herein are put into effect.

The smart grid 100 is configured to recognize unmetered loads (i.e., power diversion or theft). In one example, the techniques disclosed herein overcome transformers' inability to measure their own secondary voltages. In the example, the meters repeatedly make paired voltage and current measurements. The measurement data allows calculation of impedance at the meter as change in voltage over change in current. Using each meter's impedance, the voltage at the secondary of the transformer may be calculated. Using each meter's calculation, an average or running average calculation of the voltage at the secondary of the transformer may be calculated. Using a voltage associated with each transformer, analytic techniques within the smart grid 100 may be performed to identify transformers having a likelihood of unmetered electrical loads.

Figure 2:
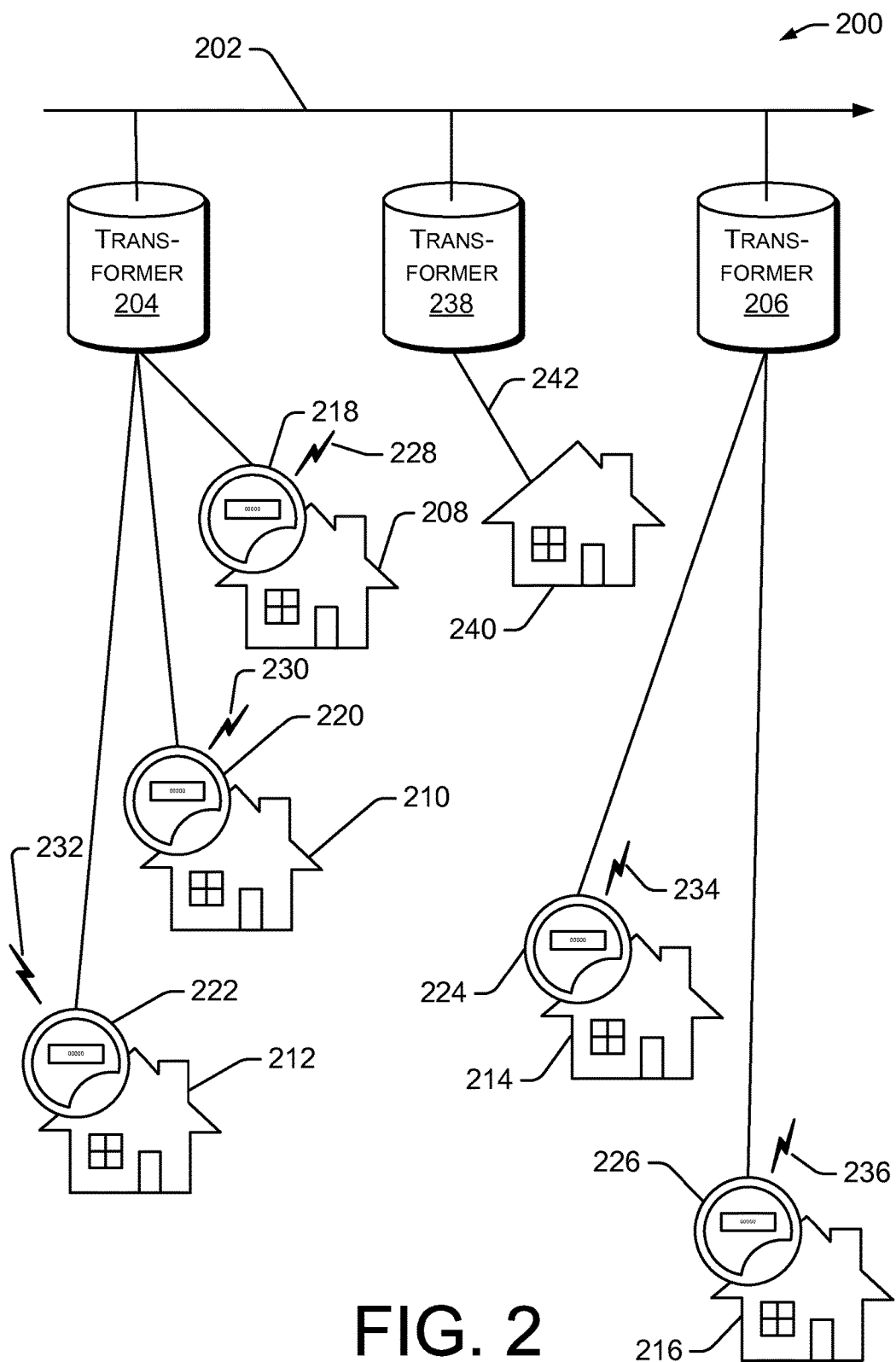
FIG. 2 is a block diagram of an example of a smart electrical grid, wherein smart meters (and/or a central or back office, as seen in FIG. 1) are configured to calculate voltages at a secondary of a plurality of transformers for use in identifying possible instances of power diversion, including by installation of an unauthorized transformer.

FIG. 2 shows an example of a smart electrical grid 200. In one aspect of the grid 200, smart meters and/or a central office are configured to identify high impedance situations. By calculating the impedance at a plurality of locations on the electrical grid 200 (e.g., at each meter) and saving data over time, techniques may be utilized to identify high impedances that result from gradual deterioration of infrastructure, rapid changes to the infrastructure and/or which were present when the techniques were implemented.

In another aspect of the grid 200, the smart meters and/or the central office are configured to identify electrical diversion (e.g., theft). In one example, analytic techniques calculate a voltage at each of a plurality of transformer secondary coils. The calculated voltage may be compared, such as by an application operable on a plurality of smart meters and/or a central or back office (as seen in FIG. 1). The comparison may be used to identify possible instances of power diversion, including unmetered loads attached to a secondary of one or more transformers, or by installation of an unauthorized transformer attached to a primary feeder that provides power to unmetered load(s).

FIG. 2 shows portions of a second example of a smart electrical grid 200. In the example shown, a primary feeder 202 provides power to transformers 204 and 206. The transformers 204 and 206 provide power to houses (or other customers) 208-216. The power provided to the houses 208-216 is measured by meters 218-226. The meters 218-226 communicate with a central office using one or more communication pathways, which may utilize RF signals 228-236 or other technology.

An unauthorized or rogue transformer 238 has also been installed on the primary feeder 202 by a bad actor. The unauthorized transformer 238 provides unmetered power to consumers at house 240 over low voltage lines 242. Thus, in the example of FIG. 1, the building 136 was connected by unauthorized secondary wiring 138 to the transformer 106. In contrast, FIG. 2 shows that bad actors have installed both a transformer 238 and also low voltage wiring 242 in an effort to divert electrical power.

The smart grid 200 is configured to recognize unmetered loads related to the installation of an unauthorized transformer. In one example, each meter at a transformer repeatedly makes paired voltage and current measurements at the meter. An impedance value of the meter is calculated as change in voltage divided by change in current of two pairs of measurements. A voltage at a transformer associated with each meter is calculated, using calculated impedance and measured voltage and current. The transformer voltages associated with each meter's data may be averaged. Using the averaged voltage for each transformer, analytic techniques within the smart grid 200 may be performed to identify, recognize and/or locate unauthorized transformers. In an example, analytic techniques may include looking for groups of transformers having lower-than-expected voltages. Such a group of transformers may be downstream (i.e., further from an electrical substation) from an unauthorized transformer. In operation, power used by the unauthorized transformer 238 may tend to lower voltages on the primary feeder 202. Accordingly, the presence of the unauthorized transformer 238 may be detected by analytic techniques which recognize lower-than-expected voltages at transformer 206.

Figure 3:
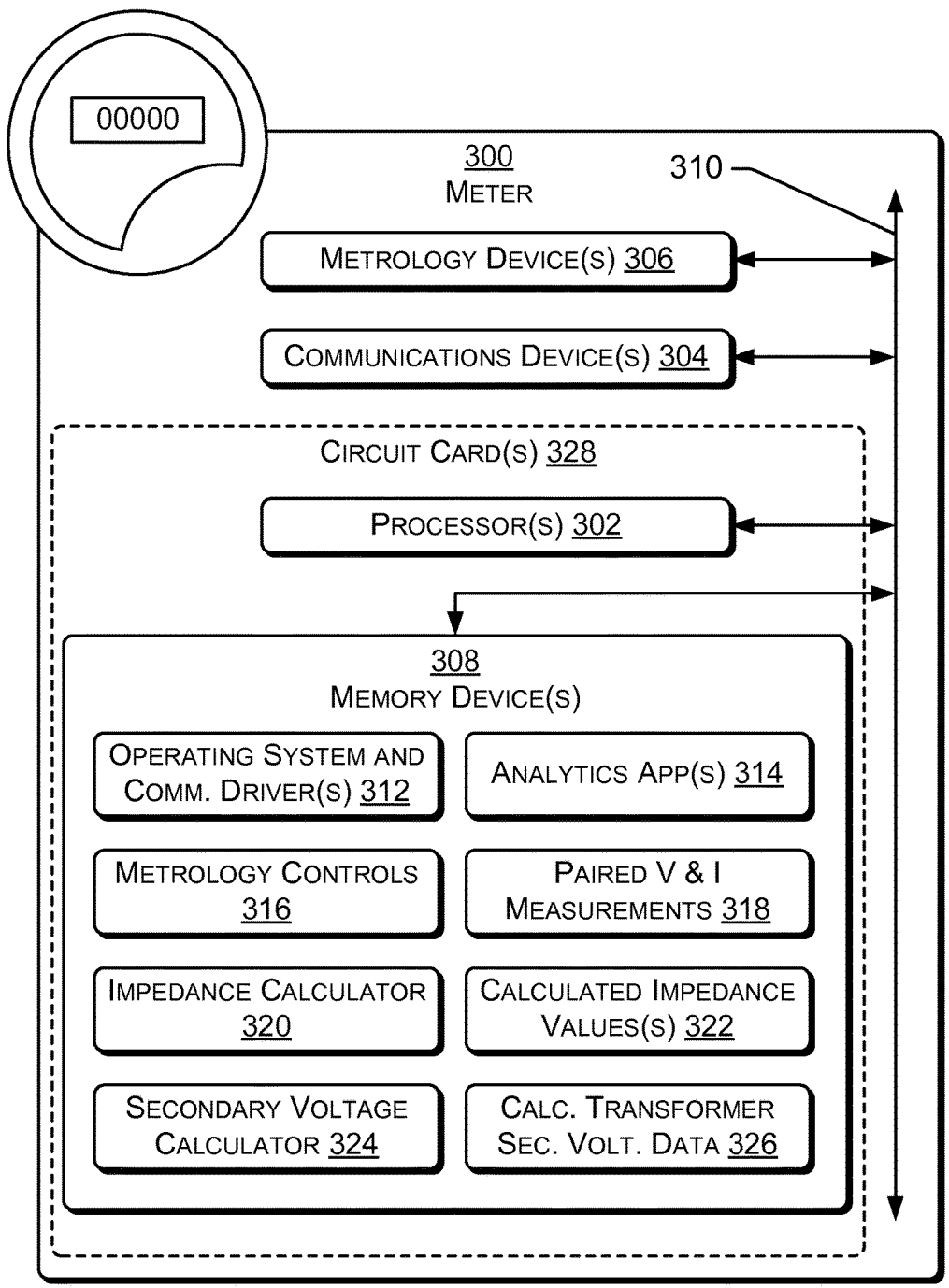
FIG. 3 is a block diagram of a smart meter showing an example smart meter, configured to detect, or assist in the detection of, high impedance wiring and/or power diversion.

FIG. 3 is an example smart meter 300, configured to detect, or assist in the detection of, high impedance wiring and/or power diversion. In the example shown, processor(s) 302, communications device(s) 304, metrology device(s) 306, and memory device(s) 308 are configured to allow communication, such as over bus, PCB board or wiring harness 310.

The meter 300 may include one or more processors 302, such as microprocessors, microcontrollers, gate arrays, etc., that are configured to execute program statements or other logical instructions. The processor(s) 302 may be in communication with one or more communications device(s) 304, such as an RF or PLC transceiver. The communication device(s) 304 may provide one- or two-way communications with other meters or smart grid nodes, to thereby form a mesh or star network, and may provide communications directly or indirectly with the central office 102 (of FIG. 1).

One or more metrology device(s) 306 may be configured to make voltage and current measurements. In one aspect, such measurements may be utilized to determine power consumption at a customer. Accordingly, the metrology device(s) 306 may obtain paired voltage and current at rapid intervals or in a generally continuous manner, for use in calculation of power consumed at a customer's site. The paired measurements may be associated with a time of measurement (e.g., a timestamp), and may be saved in the memory device 308 and/or transmitted to the head office.

One or more memory devices 308 may be configured according to any technology, such as random access, flash, disk, etc. An operating system and one or more smart grid communications driver(s) 312 may be defined on the memory device 308. Communications driver(s) may be configured to operate communications devices 304, and to communicate with other meters and/or with the central office.

One or more analytics applications 314 may perform a number of smart grid analytic techniques, some of which are describe with references made to FIGS. 5-20. Metrology controls 316 may include drivers or other software configured to operate the metrology devices 306. The metrology controls 316 may be configured to cause the metrology devices 306 to perform frequent voltage and current measurements. Such measurements may be time-stamped or otherwise provided with an indication of a time of measurement. A time series of such measurements may be stored in a data structure, such as the paired voltage and current measurements 318. The voltage and current measurements 318 may be included in the input used by one or more analytics application(s) 314. The analytics applications 314 may be configured to determine if high impedance situations exist and/or if electricity is being diverted.

An impedance calculator 320 is configured to calculate and repeatedly update calculated impedance associated with the meter 300. The calculated impedance values may be used to determine if a high impedance situation exists. The calculated impedance values may be stored in one or more data structures and/or memory devices, such as the example calculated impedance value 322 data structure shown in memory device 308. The apparent or calculated impedance at the meter, $Z_M$, is based on voltage change and current change over a short period of time, or voltage change resulting from current change over a short period of time. In the example shown, the apparent meter impedance may be obtained by analysis of two or more pairs of voltage and current change, according to the example relationship: $Z_M \approx \Delta V_M / \Delta I_M$, where one pair of measurements is a voltage measurement and a current measurement. In the relationship, the change in voltage at the meter is a present (or recent) voltage measurement minus a previous voltage measurement. Similarly, the change in current at the meter is a present (or recent) current measurement minus a previous current measurement. Thus, two paired voltage/current measurements may be used to calculate the impedance. The stored calculated impedance values 322 may be used by analytics techniques and applications 314 to determine high impedance situations and/or conditions. The calculated impedance values 322 may also be used as input in the calculation of voltages at the secondary of the transformer associated with the meter.

A secondary voltage calculator 324 may be configured to calculate voltages at a secondary of a transformer. The calculated voltages may be stored in a data structure or memory location, such as the calculated transformer secondary voltage data 326 defined in memory device 308. The calculation may be based on voltage and current measurements made by the meters associated with the transformer. The voltage at the secondary of the transformer may be calculated using the equation: $V_S - V_M = Z_M \cdot I_M$. That is, the voltage at the transformer secondary, minus the voltage at the meter, equals the impedance of the meter multiplied by the current measured by the meter. Each meter may infer the voltage at the secondary of its supply transformer by rearranging the equation as: $V_S = V_M + (Z_M \cdot I_M)$.

To calculate an estimate of the voltage at the secondary of the transformer, $V_S$, utilizing all meters associated with that transformer, the average values obtained from each meter's current, $I_M$, voltage $V_M$, and impedance, $Z_M$, may be used, for all meters M=1 . . . N on that transformer. Note that if the transformer voltage values inferred from some meters on the transformer are substantially lower than the majority, then theft or faulty wiring/infrastructure leading to high impedance at meter(s) with low inferred voltage may be suspected. However, if voltage values substantially "agree" (e.g., to within a statistical confidence level of 95%, using known statistical techniques) then a running average inferred transformer voltage, $V_S$, may be calculated.

The inferred or calculated transformer secondary voltage at multiple transformers along a same (primary) feeder is generally expected to drop along the feeder length in the direction away from the substation. This drop is more pronounced in transformers having higher loads that are more distant (i.e., further downstream) on the primary feeder.

FIG. 3 shows an optional configuration wherein a circuit card 328 may be installed in a conventional or "dumb" meter, thereby providing an upgrade path for the meter to allow the meter to participate in a smart grid and/or as part of an advanced metering infrastructure (AMI). In various examples, the circuit card 328 may be configured to include one or more of the processor 302, communications devices 304, metrology devices 306, memory devices 308 and/or other devices. The devices included in the circuit card 328 may be determined by the design requirements of a specific installation.

Figure 4:
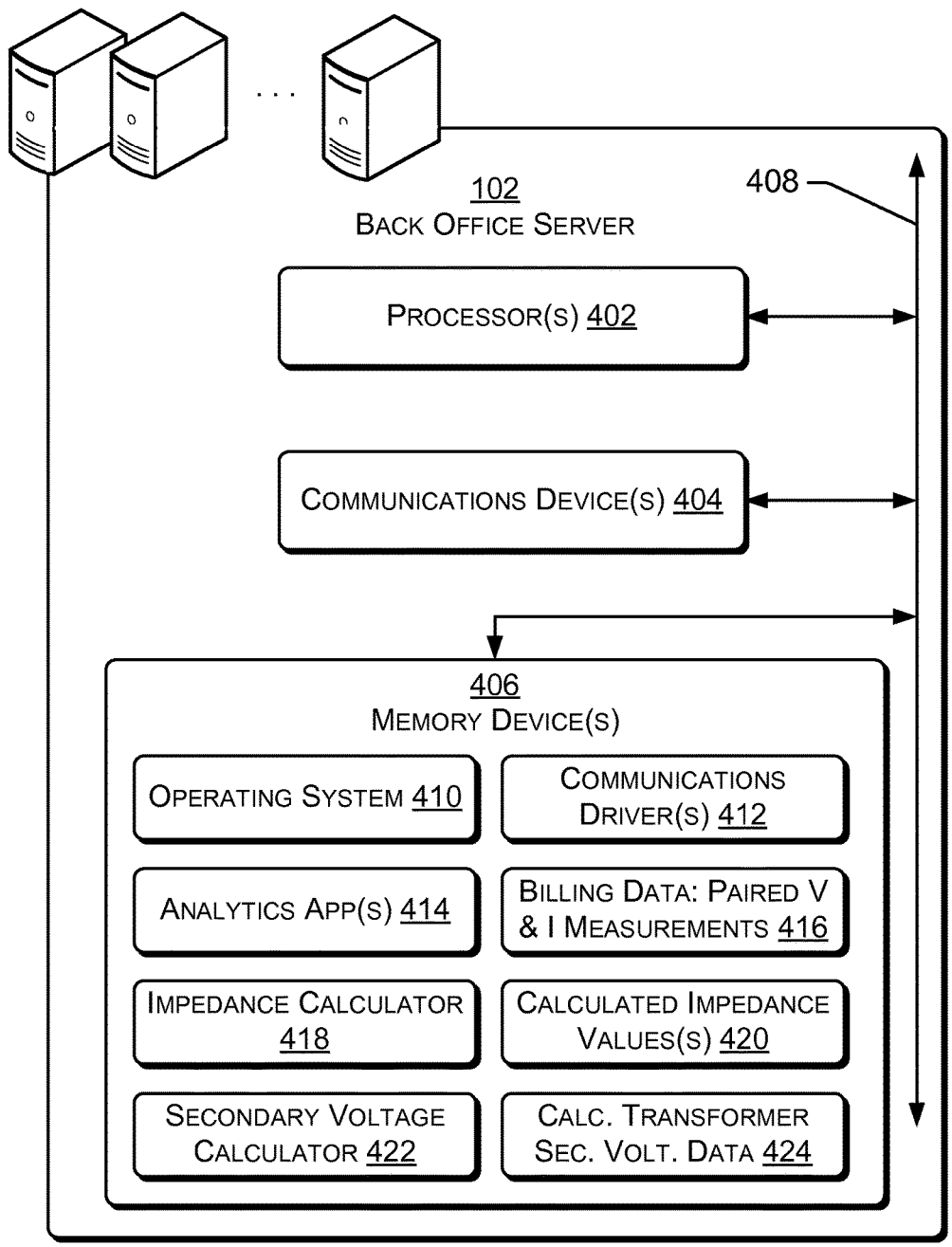
FIG. 4 is a block diagram showing example detail of a central or back office.

FIG. 4 is a block diagram showing example detail of a central or back office server 102, configured to detect, or assist in the detection of, high impedance wiring and/or power diversion. In the example shown, processor(s) 402, communications device(s) 404, and memory device(s) 406 are configured to allow communication, such as over bus, connector, or PCB board 408.

The central office server 102 may include one or more processors 402, such as microprocessors, microcontrollers, gate arrays, etc., that are configured to execute program statements or other logical instructions. The processor(s) 402 may be in communication with one or more communications device(s) 404, such as an RF or PLC transceiver. The communication device(s) 404 may provide one- or two-way communications with meters or other smart grid nodes, to thereby form a mesh or star network.

An operating system 410, communications driver(s) 412, and one or more analytics applications 414 may be defined in the one or more memory devices 406. The analytics applications 414 may be configured to perform some or all of the impedance calculations at each of a plurality of meters and to thereby identify high impedance situations. The analytics applications 414 may be configured to perform some or all of the meter impedance calculations, transformer secondary voltage calculations, and voltage comparison and analysis among transformers. Generally, the analytics applications 414 may be configured to identify possible instances of power diversion. Such instances of power diversion may include unauthorized and/or unmetered connection to a transformer secondary. Such instances may also include unauthorized connection of a transformer and unmetered load(s) to a primary distribution line. Additionally, the analytics application(s) 414 may be configured to manage, communicate and/or pass instructions and/or data to/from any of the subroutines or data stores discussed herein.

The paired voltage and current measurement data 416, impedance calculator 418, calculated impedance values 420, secondary voltage calculator 422, and calculated transformer secondary voltage data 424 may be configured in manners similar to their analogs seen in FIG. 3.

Example Methods

In some examples of the techniques discussed herein, the methods of operation may be performed by one or more application specific integrated circuits (ASIC) or may be performed by a general purpose processor utilizing software defined in computer-readable media. In the examples and techniques discussed herein, the memory 308, 406 may comprise computer-readable media and may take the form of volatile memory, such as random access memory (RAM) and/or non-volatile memory, such as read only memory (ROM) or flash RAM. Computer-readable media devices include volatile and non-volatile, removable and non-removable media implemented in any method or technology for storage of information such as computer-readable instructions, data structures, program modules, or other data for execution by one or more processors of a computing device. Examples of computer-readable media include, but are not limited to, phase change memory (PRAM), static random-access memory (SRAM), dynamic random-access memory (DRAM), other types of random access memory (RAM), read-only memory (ROM), electrically erasable programmable read-only memory (EEPROM), flash memory or other memory technology, compact disk read-only memory (CD-ROM), digital versatile disks (DVD) or other optical storage, magnetic cassettes, magnetic tape, magnetic disk storage or other magnetic storage devices, or any other non-transitory medium that can be used to store information for access by a computing device.

As defined herein, computer-readable media does not include transitory media, such as modulated data signals and carrier waves, and/or signals.

FIGS. 5-20 are flow diagrams showing example processes which are representative of techniques for use in recognizing high impedance conditions in wiring and/or connections, and for use in recognizing energy diversion. The processes are described with references to the examples and techniques of FIGS. 1-4. However, the processes may be implemented by operation of numerous other meters, servers, and systems. Additionally, the meters, servers, and systems of FIGS. 1-4 may be utilized by operation of methods not specifically discussed in FIGS. 5-20.

Figure 5:
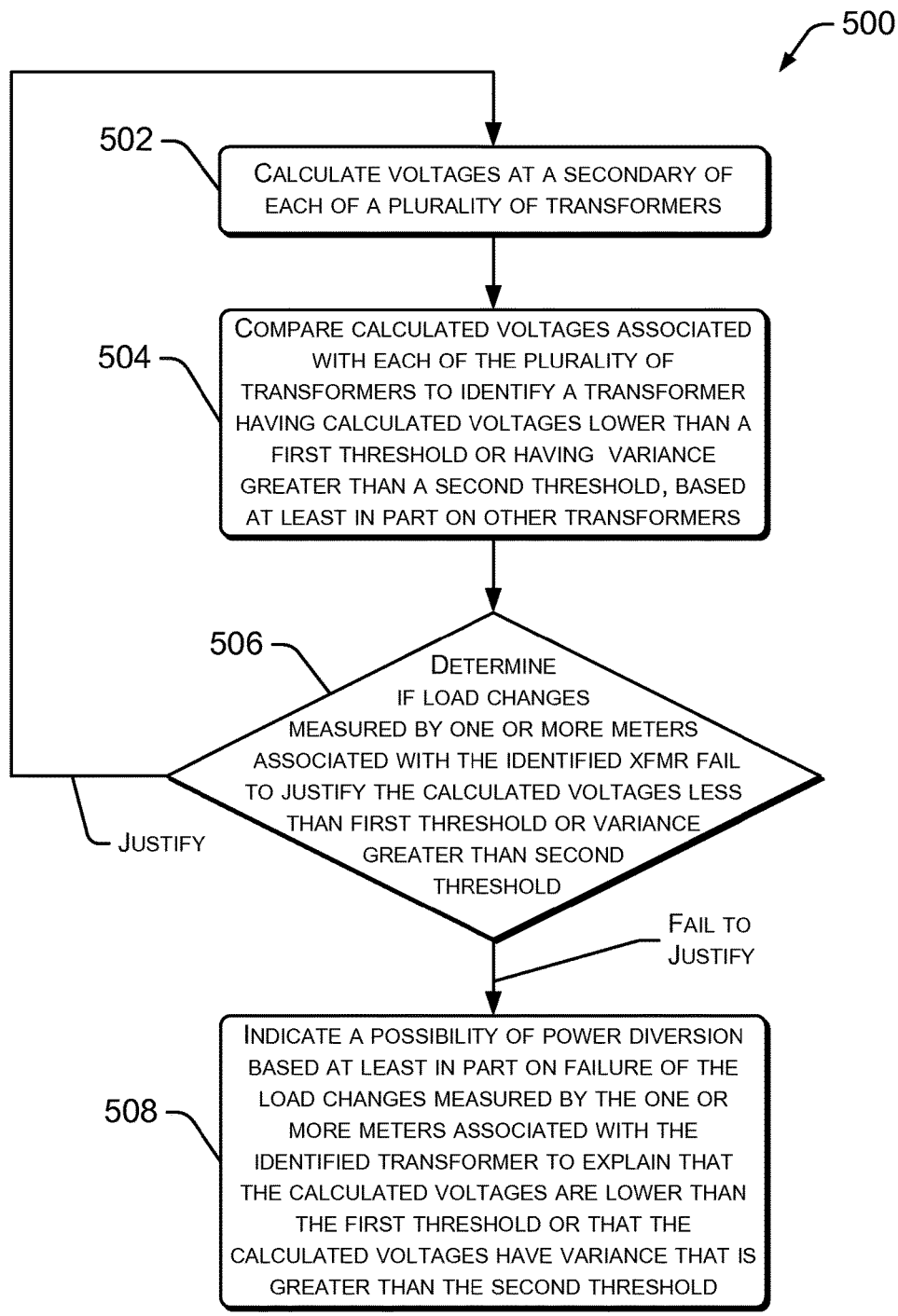
FIG. 5 is a flowchart showing a first example method by which power diversion may be detected by identifying a transformer due to lower, or intermittently lower, voltage at its secondary.

FIG. 5 is a flowchart showing a first example method 500 by which power diversion (e.g., theft) may be detected. The voltages at each of a plurality of transformer secondary windings may be calculated. In one example, successive voltage and current measurements are made at each of a plurality of meters on each transformer. Change in voltage divided by change in current may be calculated, to determine impedance at the meter. Impedance, voltage, and current at each meter can be used to calculate voltage at the secondary, and plural meters' estimates of the secondary voltage can be averaged. Transformers with voltages that are lower or more variable than expected may be identified. If a particular transformer is identified, the meters associated with that transformer are examined to determine if current measurements by the meters explain the transformer's voltage levels and/or voltage level variance. Power diversion may be indicated, if current use at the transformer's meters do not explain the transformer's voltage levels and/or voltage level variance.

At block 502, a voltage at a secondary of each of a plurality of transformers is calculated. The voltage and current, $V_M$ and $I_M$, at each meter may be calculated as the difference between successive measurements. Impedance at the meter, $Z_M$, may be calculated as the ratio of these values. The voltage at the secondary of the transformer, $V_S$, may be calculated using the equation: $V_S = V_M + (Z_M \cdot I_M)$, wherein $V_S$ may be the average, or a running average, of several meters associated with the transformer.

At block 504, the calculated voltages associated with each of the plurality of transformers may be compared. The comparison may identify at least one transformer having calculated voltages that are lower than a first threshold or having calculated voltages that have variance greater than a second threshold. The identification may be based at least in part on calculated voltages of a plurality of transformers.

At block 506, it is determined whether load changes, measured by one or more meters associated with the identified transformer, can justify the calculated voltages being less than a first threshold or voltage variances being greater than a second threshold. If load changes can justify the magnitude and/or variance of the calculated voltages, power diversion is not indicated. In an example, unusual loads and/or unusual load changes experienced at one or more meters associated with a transformer may result in the unusual voltages at a secondary of the transformer. However, if measured load changes at meters associated with the transformer fail to justify the calculated voltages at the transformer, then at block 508, a possibility of power diversion is indicated or transmitted.

At block 508, a possibility of power diversion may be indicated (transmitted, displayed, etc.) if the load changes are not present that would explain that the calculated voltages are lower than the expected range. The indication may result in dispatch of a work crew to investigate the possible diversion. In a first example, the possibility of power diversion is indicated based at least in part on a calculated voltage that is less than a first threshold, or by voltage variance that is greater than a second threshold. The possibility of power diversion may also be based at least in part on failure of load changes, measured by one or more meters associated with the identified transformer, to explain the calculated voltage that is lower than the expected range. In an example, a substantial load may result in voltage measurements below the first threshold. Accordingly, the substantial load explains the lower-than-expected transformer voltages. In another example, varying loads measured by one or more of a transformers' meters may result in voltage variance greater than the second threshold, thereby explaining the varying transformer voltages.

Figure 6:
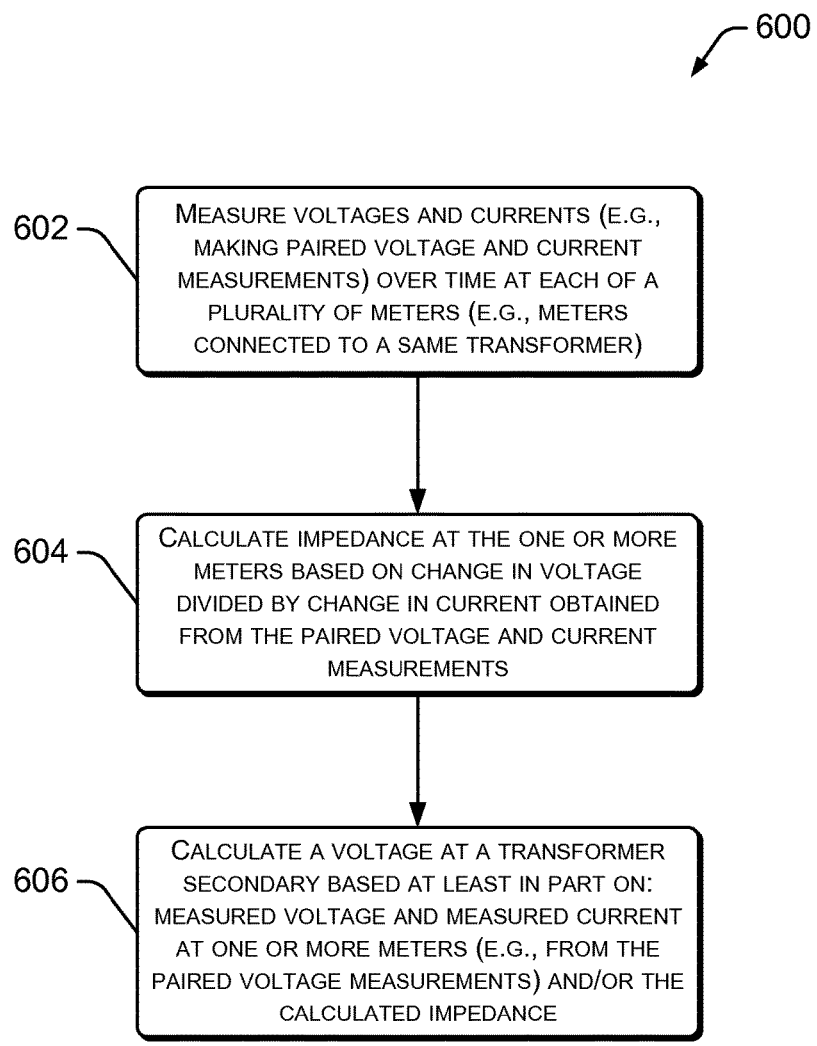
FIG. 6 is a flowchart showing several example techniques by which the voltage at the secondary of a transformer may be calculated.

FIG. 6 shows several example techniques 600 by which the voltage at the secondary of a transformer (e.g., as discussed with respect to block 502 in FIG. 5) may be calculated. To calculate the secondary transformer voltage, the several example techniques shown in the several blocks of FIG. 6 may optionally be used individually or in various combinations of two of more of the techniques.

At block 602, voltages and currents (e.g., paired voltage and current measurements) may be measured over time at each of a plurality of meters (e.g., meters connected to a same transformer).

At block 604, impedance at the one or more meters may be calculated based at least in part on change in voltage divided by change in current obtained from the paired voltage and current measurements. In one example, the impedance at a meter may be calculated as $Z_M \approx \Delta V_M / \Delta I_M$, where $\Delta V_M$ is the difference between two voltage measurements at the meter and $\Delta I_M$ is the difference between two current measurements at the meter.

At block 606, a voltage may be calculated at a transformer secondary based at least in part on: measured voltage and measured current at one or more meters (e.g., from the paired voltage measurements) and/or the calculated impedance. In one example, the voltage at the transformer secondary, $V_S$, may be calculated as $V_S = V_M + (Z_M \cdot I_M)$.

Figure 7:
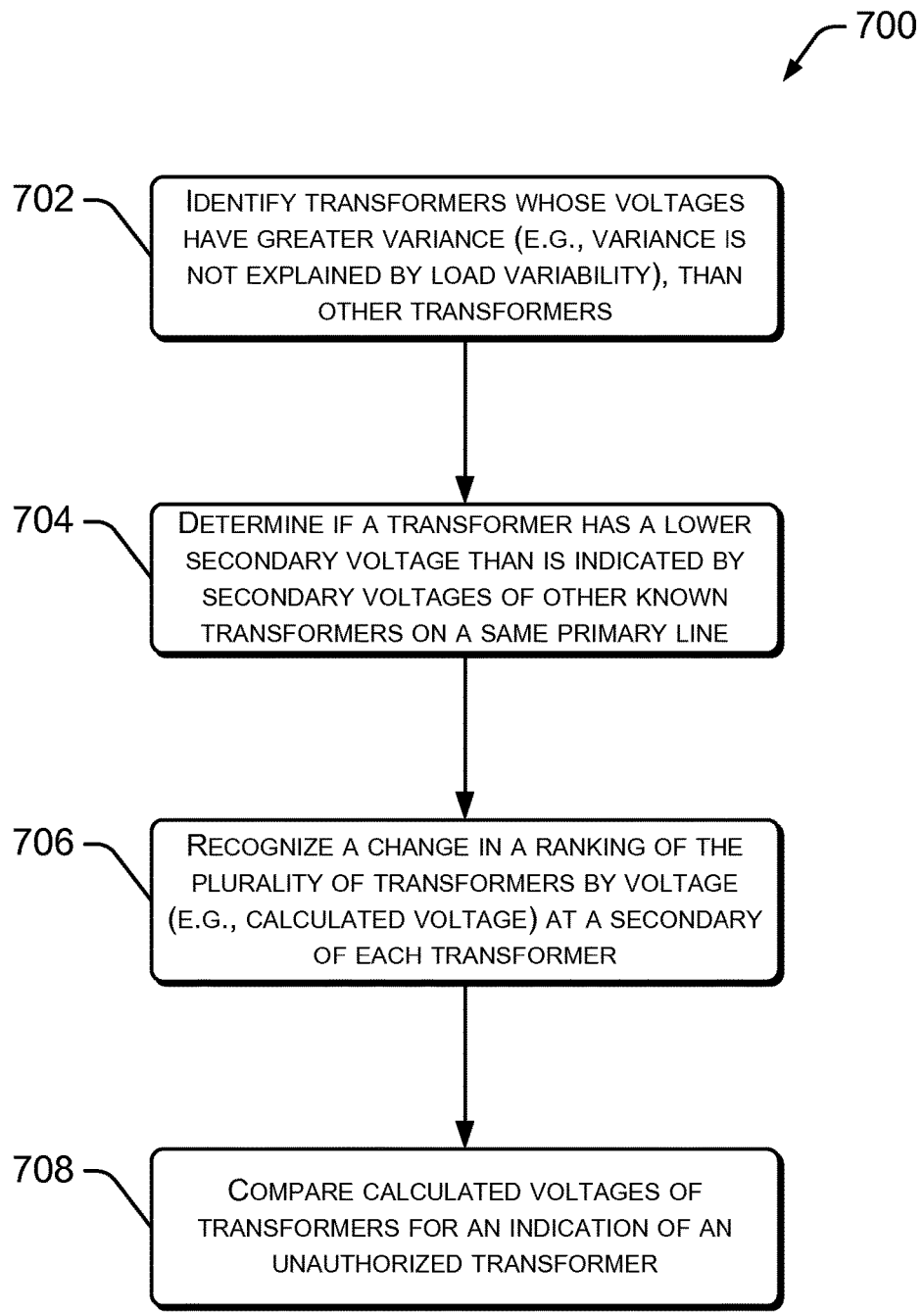
FIG. 7 is a flowchart showing several example techniques by which the calculated voltages associated with each of the plurality of transformers may be compared.

FIG. 7 shows several example techniques 700 by which the calculated voltages associated with each of the plurality of transformers may be compared. Accordingly, optional detail associated with block 504 in FIG. 5 is described. To compare the voltages, the several example techniques shown in the several blocks of FIG. 7 may optionally be used individually or in various combinations of two or more of the techniques.

At block 702, transformers whose secondary voltages have greater variance than other transformers may be identified. In particular, the transformers may be identified when the variance of the voltage at the transformer's secondary is not explained by load variability. That is, a transformer having a metered load that is stable, but whose secondary voltage has more than a threshold level of variability may also have an unmetered load associated with it. In this case, the unmetered load may cause the secondary voltage of the transformer to vary. A metered load may also cause variance in a transformer's secondary voltage. However, metered changes in current would explain the changes in voltage at the secondary. By comparing transformer secondary voltages of a plurality of transformers, an appropriate threshold of variability may be determined, and transformers having voltage variability exceeding that threshold may be flagged for investigation for possible electrical diversion.

At block 704, depending on voltage support techniques utilized by an electrical grid, downstream transformers may have slightly lower voltages than transformers closer to a substation. However, voltage falloff that is greater than predicted can indicate the installation of an unauthorized transformer on a primary high voltage line. Such an unauthorized transformer was not considered in the design of the electrical grid, and may cause transformers downstream to have voltages that are lower-than-expected. According to the techniques of block 704, it is determined if a transformer has a lower secondary voltage than is indicated by secondary voltages of other known transformers on a same primary line (e.g., a high voltage feeder line). That is, while some voltage falloff may be expected (depending on voltage support devices known to be used), excessive voltage falloff of downstream transformers may indicate installation of an unauthorized transformer and unmetered load(s). The unauthorized transformer may be installed upstream from the transformers having low voltage conditions.

At block 706, a change in a ranking of a plurality of transformers by voltage may be recognized. The secondary voltages associated with several transformers on a primary feeder (high voltage line) may be ranked. The secondary voltages may be measured (if such facilities exist) or calculated, such as by techniques described herein. This ranking may be fairly stable. That is, during operation one or more of the transformers may typically have a little higher voltage, and other transformers may have a little lower voltage. If the ranking changes, this may indicate unmetered electrical diversion. Such diversion is more likely if not explained by load changes (as described with reference to block 506 of FIG. 5 and other locations).

At block 708, calculated voltages of a plurality of transformers, possibly all on a same primary feeder line, may be compared. Such a comparison may indicate voltage changes that indicate the possible presence of an unauthorized transformer on the feeder line. In particular, low voltages and/or voltage variability of transformers may indicate the presence of unauthorized transformers and/or unmetered loads on authorized transformers.

Figure 8:
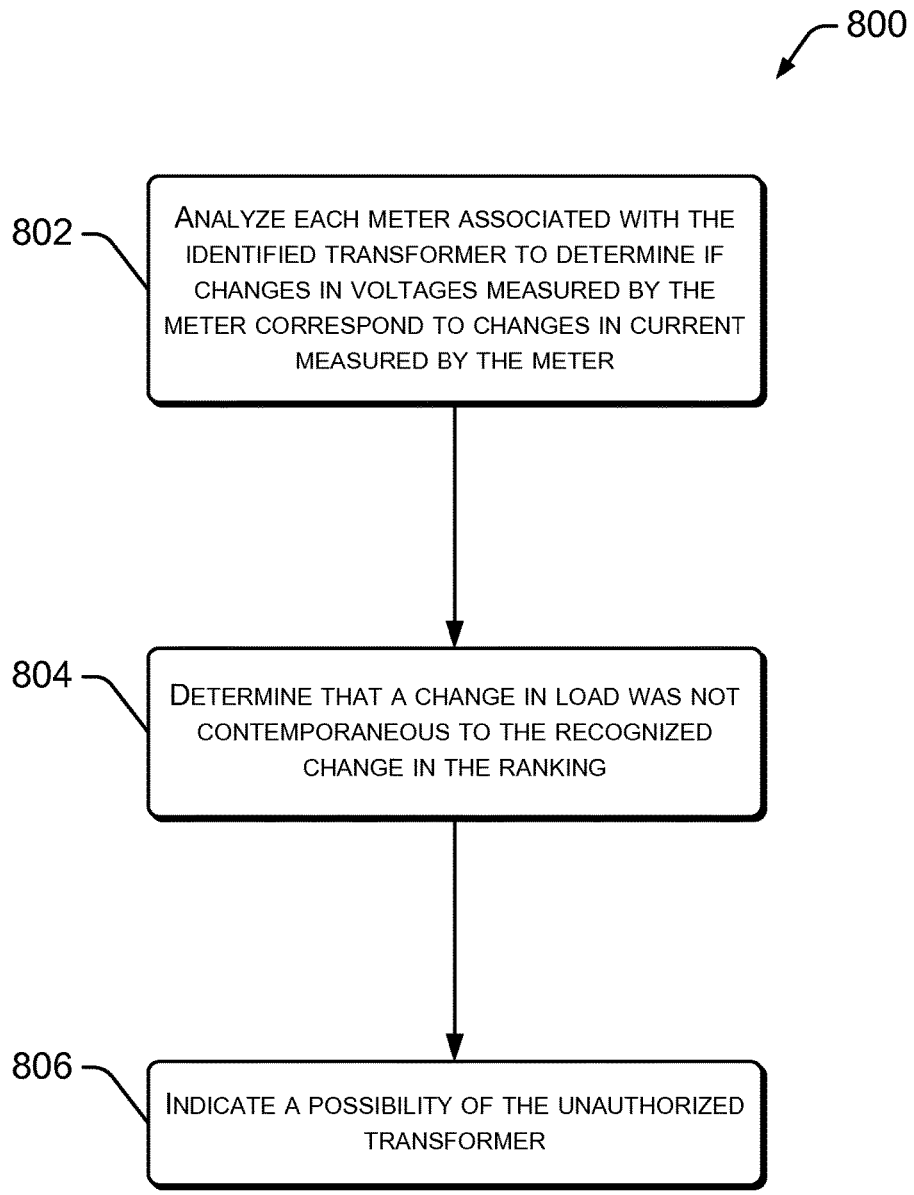
FIG. 8 is a flowchart showing several example techniques by which it may be determined whether load changes explain calculated voltages less than a first threshold or voltage variances greater than a second threshold.

FIG. 8 shows several example techniques 800 by which it may be determined whether load changes, measured by one or more meters associated with an identified transformer, can justify calculated voltages being less than a first threshold or voltage variances being greater than a second threshold. Accordingly, optional detail associated with block 506 in FIG. 5 is described. To determine if load changes were a cause of voltage anomalies at a transformer, the several example techniques shown in the several blocks of FIG. 8 may optionally be used individually or in various combinations of two of more of the techniques.

At block 802, a transformer has been identified (such as by block 504 of FIG. 5) based on techniques for the recognition of voltage abnormalities. The identified transformer is suspected of supplying power to an unmetered load. In one example, each meter associated with the transformer is analyzed. The analysis may determine if changes to the transformer's secondary were contemporaneous with changes in current measured by meters associated with the transformer. The analysis may determine if changes in voltages measured by the meter correspond to changes in current measured by the meter. That is, current use changes by a customer associated with the meter may cause a momentary voltage change at the meter and at the transformer secondary. Thus, when the customer turns on a large load, the voltage dips slightly; and the reverse when the load is turned off. If the voltages measured by each meter associated with the identified transformer do not correspond to current use measured by the meter, then the transformer may have been properly flagged as being associated with electrical diversion.

At block 804, it is determined if a change in load was or was not contemporaneous to a recognized change in a ranking (e.g., by secondary voltage) of several transformers on a same primary feeder line. If the change in load was contemporaneous to the change in the ranking, then the load change could have result in the change in the ranking. Because the load change happened (and was metered), the change in ranking is less likely to indicate theft, and more likely to be a result of the load change. However, if no load change is found among the meters of a transformer that changed within a ranking of other transformers, it is possible that the change in ranking was due to an unmetered load on the transformer.

At block 806, a possibility of the unauthorized transformer may be indicated. At block 508 of FIG. 5, a possibility of power diversion was indicated. This indication may be refined, if the evidence indicates that an unauthorized transformer may have been attached to a primary feeder line.

Figure 9:
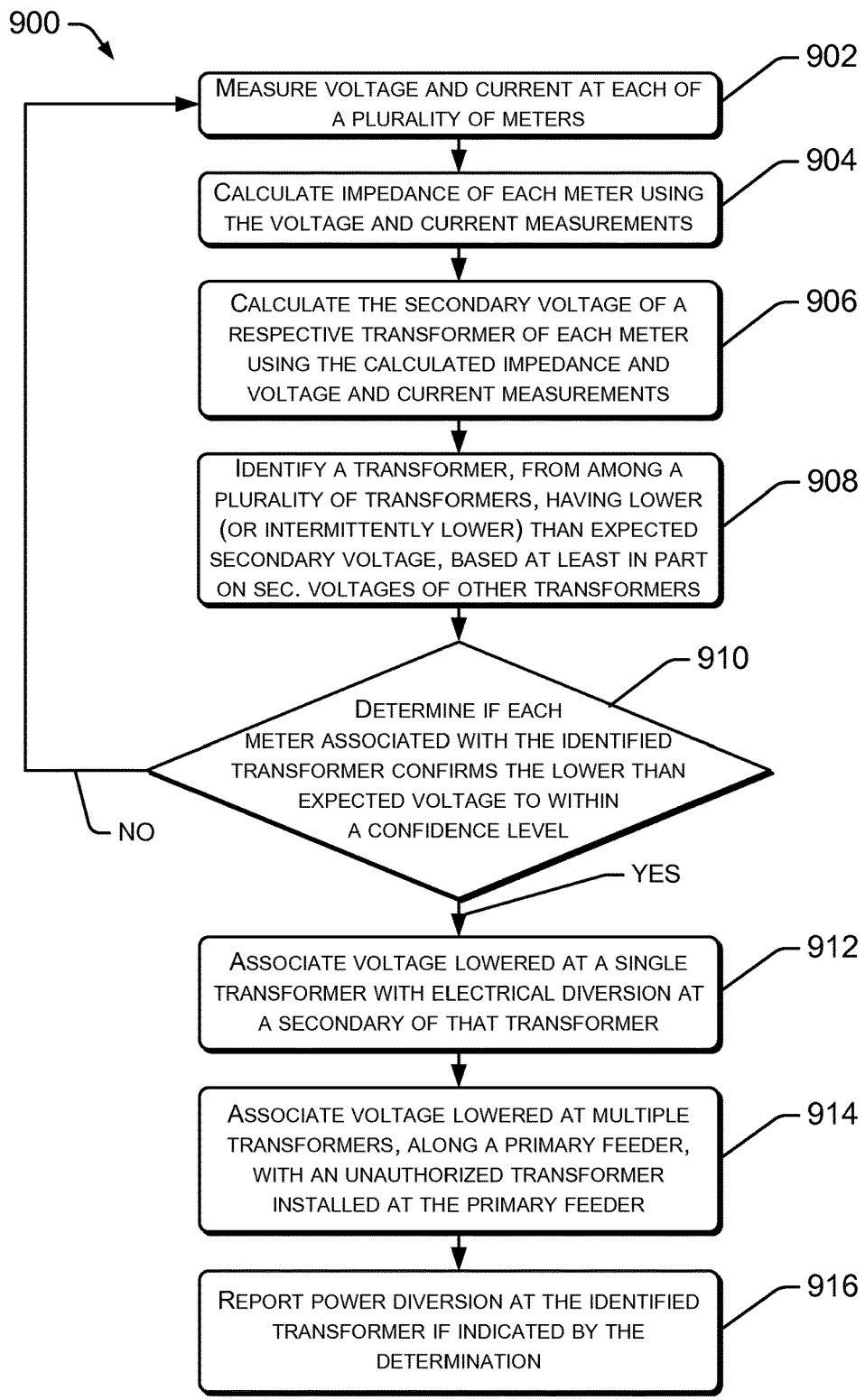
FIG. 9 is a flowchart showing a second example method by which power diversion may be detected by identifying a transformer due to lower, or intermittently lower, voltage at its secondary.

FIG. 9 shows a second example method 900 by which power diversion may be detected by identifying a transformer due to lower, or intermittently lower, voltage at its secondary. Having been identified, the transformer is suspected of providing power to unmetered loads, or of being on a primary feeder line used by an unauthorized transformer. As a step to confirm or deny this suspicion, meters associated with the identified transformer are evaluated, to determine if metered loads adequately explain the transformer voltages seen.

At block 902, voltage and current may be repeatedly measured at each of a plurality of meters. The voltage and current measurements may be made in pair, and may be made by metrology device(s) 306 seen in FIG. 3. The voltage and current measurements may be stored in pairs, such as in the data structure 318 seen in FIG. 3. The paired voltage and current measurements may be used to measure power at each meter, to calculate impedance at the meter, to calculate voltage at a transformer secondary to which the meter is attached, and to verify whether theft is indicated by unmetered loads or unauthorized transformers.

At block 904, impedance may be calculated at each meter using the voltage and current measurements. The impedance may be calculated using two pairs of voltage/current measurements. The impedance may be calculated according to $Z_M \approx \Delta V_M / \Delta I_M$, such as by the impedance calculator 320 of FIG. 3.

At block 906, the secondary voltage of a respective transformer of each meter may be calculated. The calculation of the transformer secondary voltage may be made using the calculated impedance and voltage and current measurements, according to $V_S = V_M + (Z_M \cdot I_M)$.

At block 908, a transformer may be identified, from among a plurality of transformers, having lower (or intermittently lower) than expected secondary voltage. The identification may be based at least in part on secondary voltages of other transformers. In one example, the identified transformer may change its position within a voltage ranking of transformers. In another example, the identified transformer may have a lower-than-expected, or threshold, voltage and/or have voltage variance greater than a threshold.

At block 910, it is determined whether each meter associated with the identified transformer confirms the lower-than-expected transformer secondary voltage, or intermittently lower-than-expected voltage, to within a confidence level. The determination may be made statistically, to a desired confidence threshold value. Such a confirmation of the lower-than-expected transformer voltage may be made by verifying that each meter has strong correlation between voltage change and current change. That is, voltage changes that are not accompanied by corresponding current changes tend to indicate the presence of an unmetered load.

At block 912, in one example, voltage lowered at a single transformer may be associated with, or used as an indicator for, electrical diversion at a secondary of that transformer. Thus, if a primary feeder line has several transformers, and one of the transformers has a lower-than-expected secondary voltage, this may indicate that an unmetered load is attached to the transformer.

At block 914, in a further example, voltage lowered at multiple transformers along a primary feeder line may be associated with, result from, or be used as an indicator of, the installation of an unauthorized transformer and associated unmetered loads. In one example, the unauthorized transformer may pull down transformer secondary voltages of several transformers due to loads unknown to the electrical grid managers associated with the unauthorized transformer.

At block 916, power diversion may be reported at the identified transformer if indicated by the determination at block 910.

Figure 10:
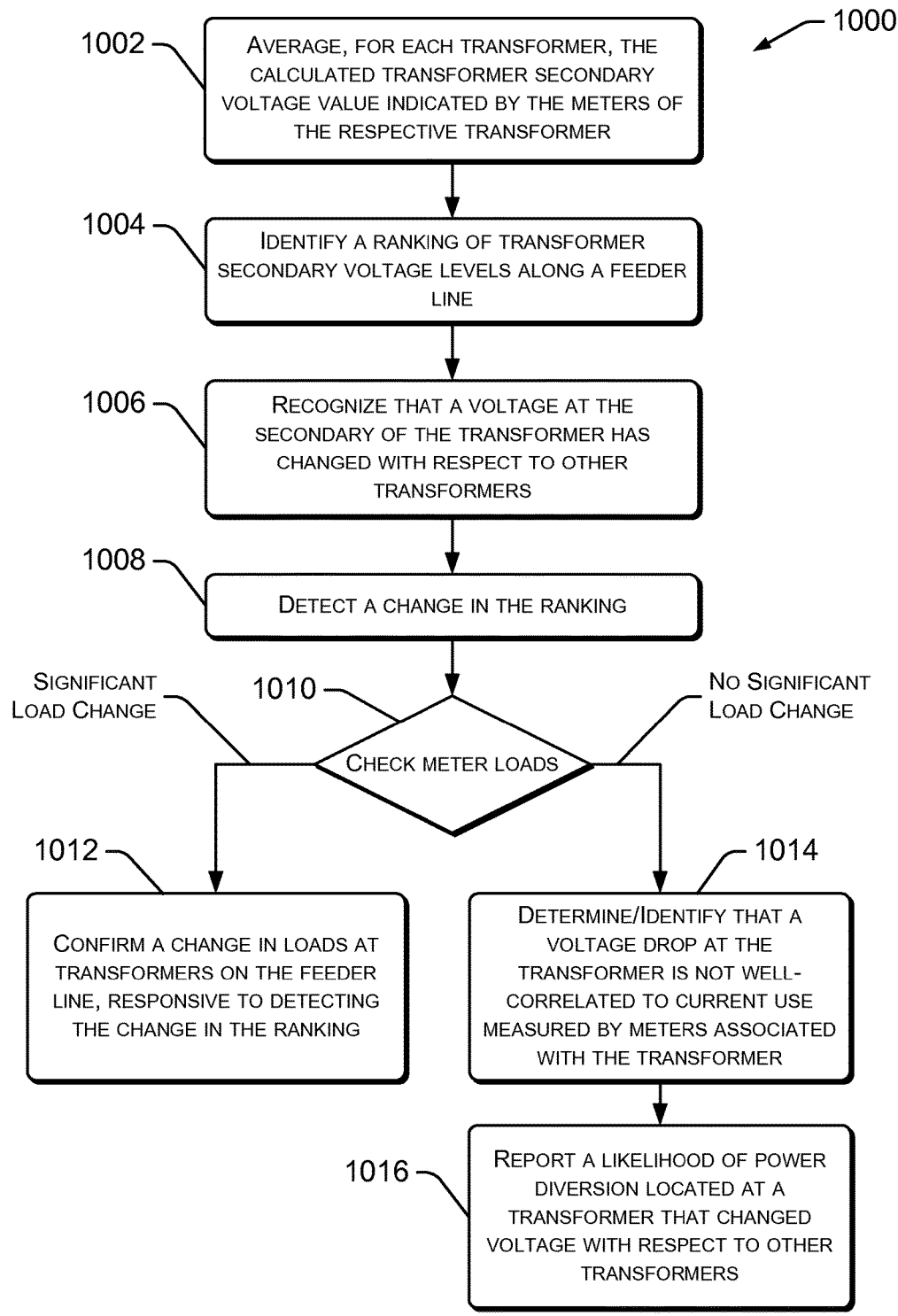
FIG. 10 is a flowchart showing several example techniques by which a transformer that is associated with electrical diversion may be identified.

FIG. 10 shows several example techniques 1000 by which a transformer that is associated with electrical diversion may be identified. In one aspect, FIG. 10 shows optional detail associated with block 908 in FIG. 9. Accordingly, FIG. 10 describes techniques that may be used to identify a transformer that has lower voltage, or intermittently lower voltage, than is expected or indicated by threshold values. The several example techniques shown in the several blocks of FIG. 10 may optionally be used individually or in various combinations of two of more of the techniques, as indicated by particular aspects of a particular electrical grid.

At block 1002, the transformer secondary voltage values calculated by each meter associated with a transformer may be averaged to provide that transformer's secondary voltage value.

At block 1004, a ranking of transformers by their secondary voltage levels may be identified along a feeder line. At block 1006, it is recognized that a voltage at the secondary of the transformer has changed with respect to other transformers. At block 1008, a change in the ranking of the transformers is detected.

At block 1010, meter loads are checked, to see if a change in a metered load resulted in the change in the ranking.

At block 1012, a change in loads at transformers on the feeder line is confirmed. The change in the loads provides a non-theft related reason for the change in the ranking of the transformers by secondary voltage that was detected at block 1008.

Alternatively, at block 1014, the voltage change (e.g., drop) that was identified was not well-correlated to current use measured by meters associated with the transformer. That is, measured current did not cause the voltage drop, leaving open the concern that unmeasured current caused the voltage drop. Accordingly, at block 1016, a likelihood of power diversion is reported. The power diversion may be taking place at or near the transformer that changed voltage with respect to other transformers.

Figure 11:
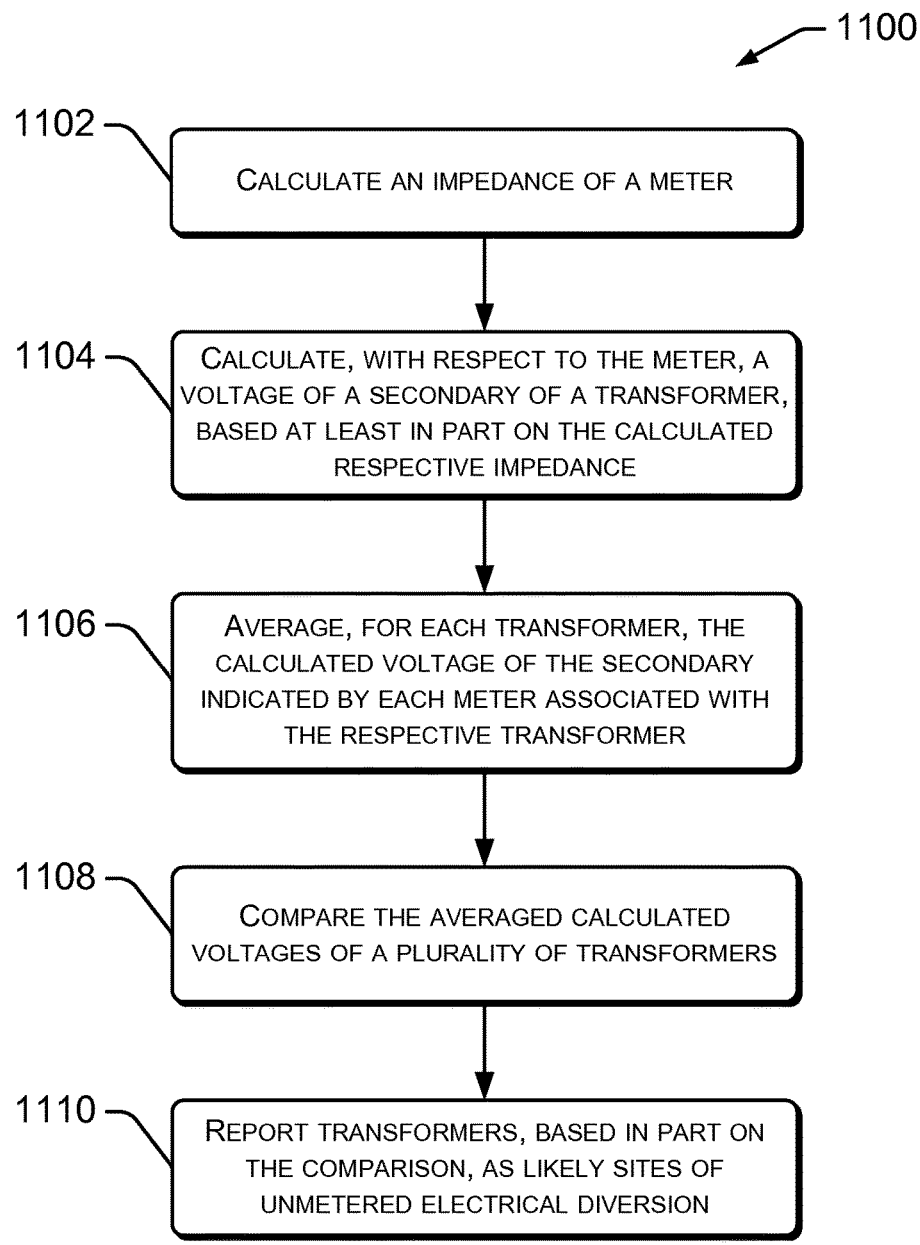
FIG. 11 is a flowchart showing a third example method by which power diversion may be detected.

FIG. 11 is a flowchart showing a third example method 1100 by which power diversion may be detected. At block 1102, an impedance of each meter may be calculated. At block 1104, for each meter, a voltage of a secondary of a transformer may be calculated. The calculation may be based at least in part on the calculated respective impedance. At block 1106, for each transformer, the calculated voltage of the transformer secondary, indicated by each meter, is averaged. At block 1108, the averaged calculated voltages of a plurality of transformers may be compared. At block 1110, transformers may be selected, based in part on the comparison, as likely sites of unmetered electrical diversion.

Figure 12:
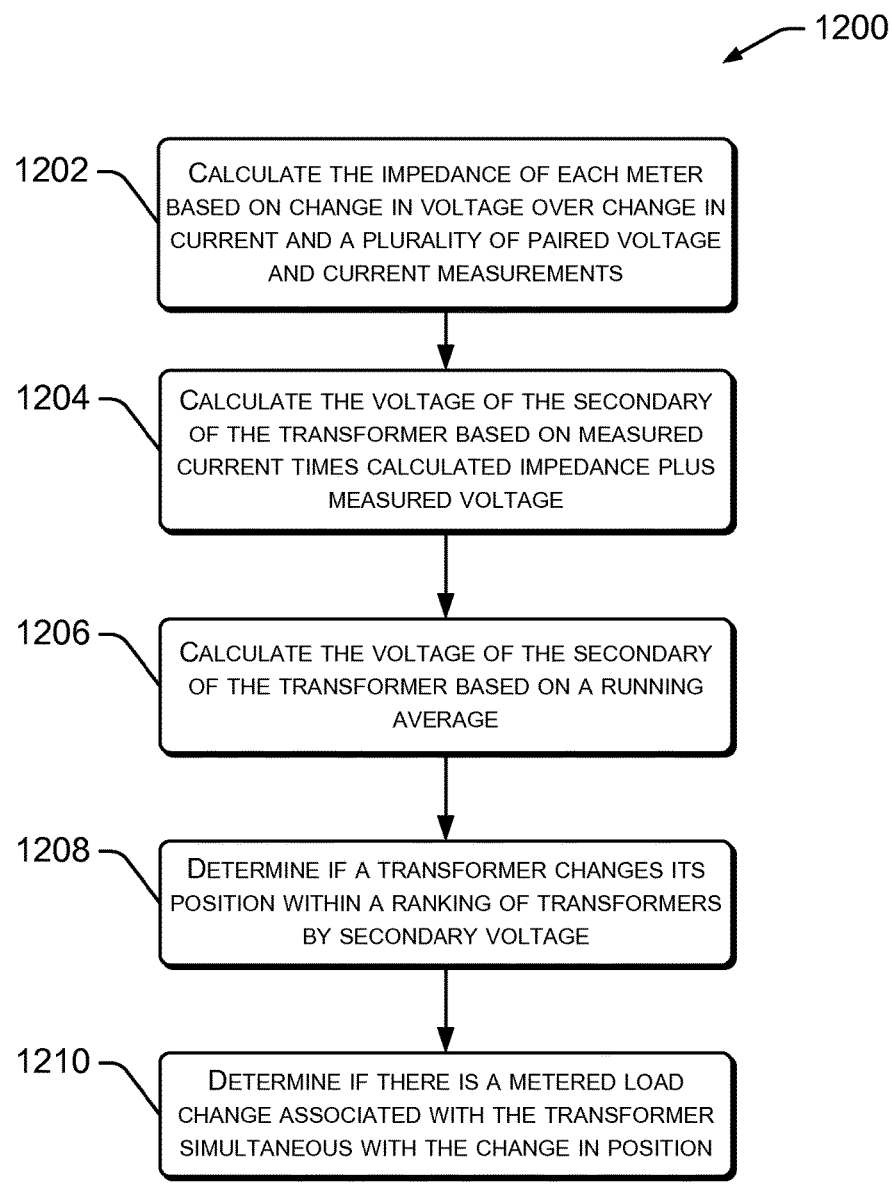
FIG. 12 is a flowchart showing several example techniques by which meter impedances, transformer voltages and transformer voltage changes are calculated and/or used.

FIG. 12 shows several example techniques 1200 by which meter impedances, transformer voltages and transformer voltage changes are calculated and/or used. Accordingly, optional detail associated with FIG. 11 is described. In the course of various calculations, the several example techniques shown in the several blocks of FIG. 12 may optionally be used individually or in various combinations of two of more of the techniques. At block 1202, the impedance of each meter may be calculated based on change in voltage over change in current and a plurality of paired voltage and current measurements. At block 1204, the voltage at the secondary of a transformer is calculated. The calculation may be based on voltage and current measurements made by one or more meters. In one example, the transformer secondary voltage may be calculated as the measured current multiplied by calculated impedance, plus measured voltage. At block 1206, the voltage of the secondary of the transformer may be calculated based on a running average. Thus, several meters' calculated transformer secondary voltages may be averaged, and a running average may be used to provide a voltage value that is both stable and up to date. At block 1208, it is determined whether a transformer changes its position within a ranking of transformers by secondary voltage. The change in position may be due to voltage changes that are caused by metered current changes or due to unmetered current changes. At block 1210, it is determined if a metered (measured) load change, which is associated with the transformer that changed its position relative to other transformers, is simultaneous with the change in position.

Figure 13:
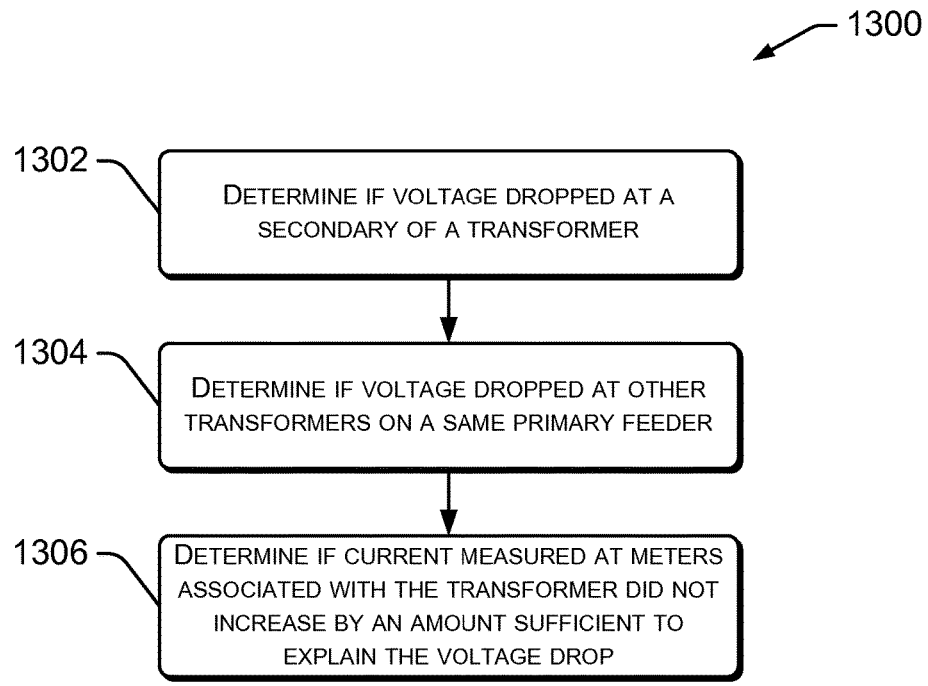
FIG. 13 is a flowchart showing several example techniques by which the calculated secondary voltages of a plurality of transformers may be compared.

FIG. 13 shows several example techniques 1300 by which the calculated secondary voltages of a plurality of transformers may be compared. Accordingly, optional detail associated with block 1108 in FIG. 11 is described. To compare transformers' secondary voltages, the several example techniques shown in the several blocks of FIG. 13 may optionally be used individually or in various combinations of two of more of the techniques.

At block 1302, it is determined that the voltage has dropped at a secondary of a transformer. If voltage drops at a transformer, and if that voltage drop was not contemporaneous with a measured current increase, then theft could be indicated. At block 1304, it is determined whether voltage dropped at other transformers on a same primary feeder. If voltage drops at several transformers, this could indicate the operation of a non-authorized transformer attached to the same primary feeder line. At block 1306, it is determined whether current measured at meters of the transformer increased by an amount sufficient to explain the voltage drop.

Figure 14:
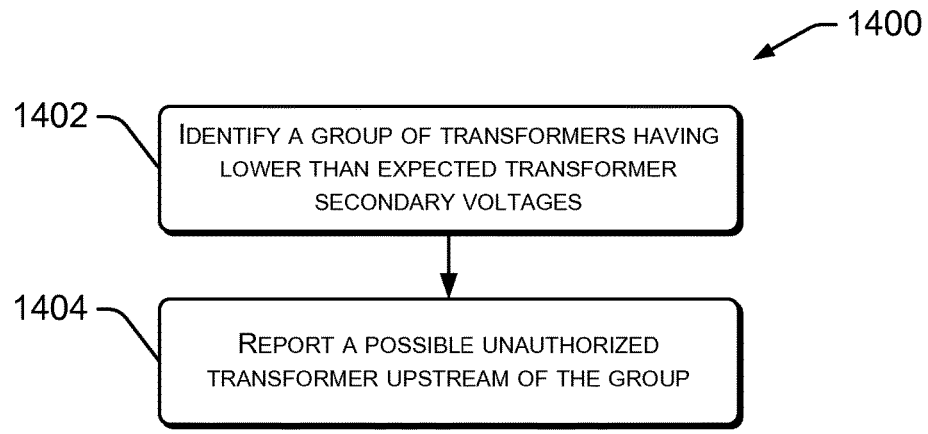
FIG. 14 is a flowchart showing several example techniques by which electrical diversion or theft may be identified.

FIG. 14 shows several example techniques 1400 by which electrical diversion or theft may be identified. Accordingly, optional detail associated with previous figures is described. The several example techniques shown in the several blocks of FIG. 14 may optionally be used individually or combination. At block 1402, a group of transformers having lower-than-expected transformer secondary voltages is identified. The voltage may be lower or intermittently lower. At block 1404, a possible unauthorized transformer upstream of the group may be reported.

Figure 15:
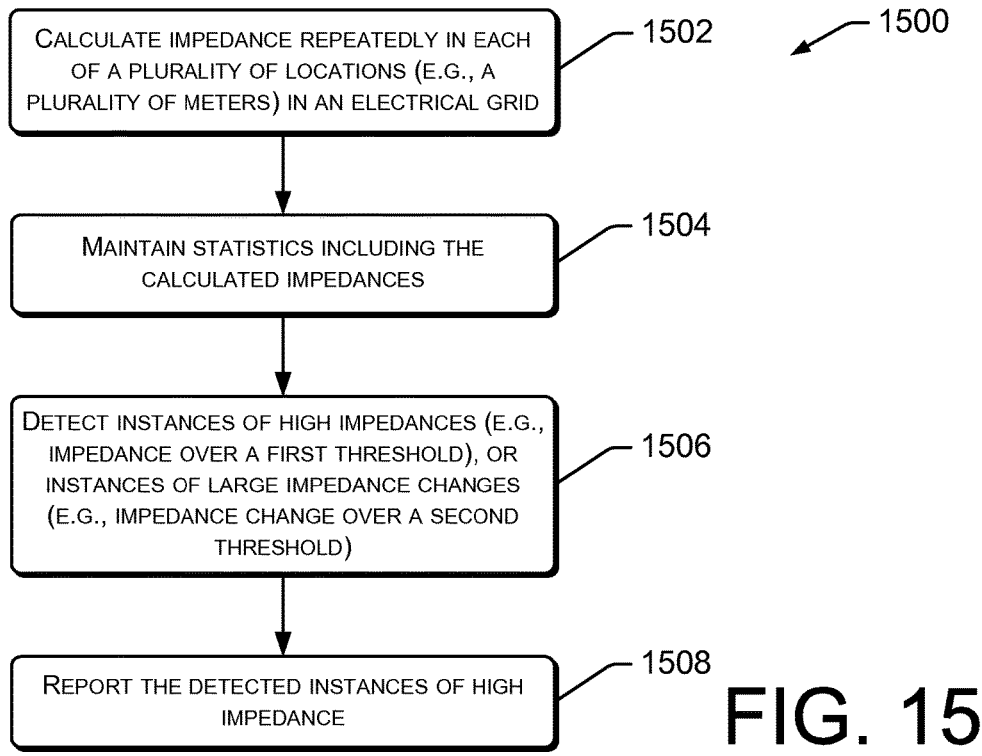
FIG. 15 is a flowchart showing an example method by which instances of high impedance wiring and/or connections may be detected.

FIG. 15 shows an example method 1500 by which instances of high impedance wiring and/or connections may be detected. At block 1502, an impedance in each of a plurality of locations (e.g., electric meters) in an electrical grid may be calculated. The calculations may be performed repeatedly, using updated current and voltage measurements. The impedance calculations may be performed as a change in two voltage measurements divided by a change in two current measurements. At block 1504, statistics may be maintained that include the calculated impedances. At block 1506, instances of high impedances may be detected. The high impedances may be defined with respect to a threshold. In one example, the impedances of the maintained statistics may be examined. At block 1508, the detected instances of high impedance may be reported, such as to a utility company head office, repair department, or other authorities.

Figure 16:
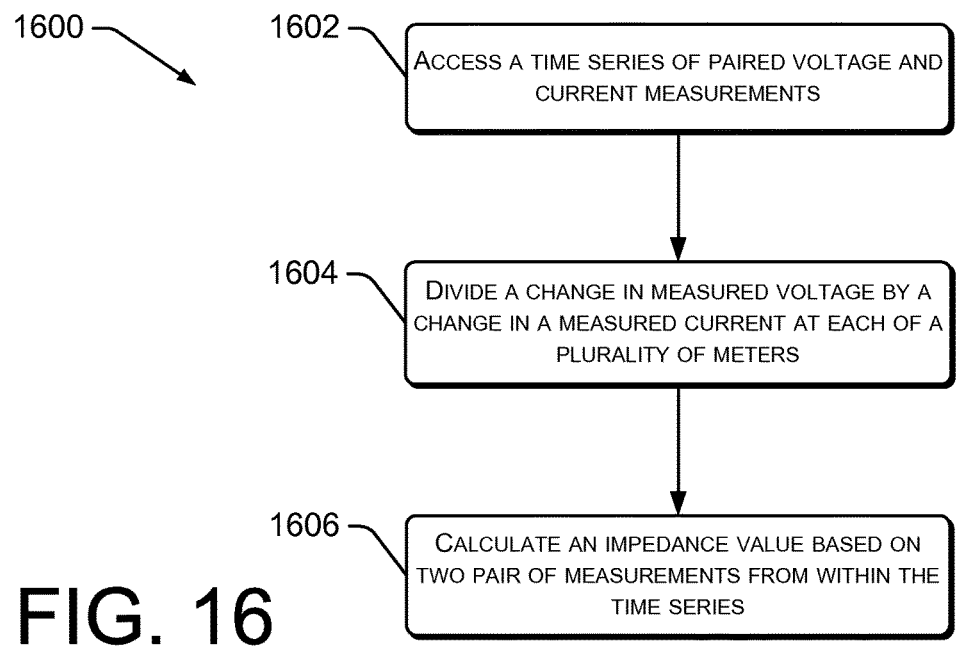
FIG. 16 is a flowchart showing example techniques by which instances of high impedance may be recognized.

FIG. 16 shows example techniques 1600 by which instances of high impedance (impedance over a threshold) may be recognized. FIG. 16 also shows example techniques by which instances of impedance change over a threshold may be detected. Accordingly, optional detail associated with block 1506 in FIG. 15 is described. To recognize high impedance, the several example techniques shown in the several blocks of FIG. 16 may optionally be used individually or in various combinations of two of more of the techniques.

At block 1602, a time series of paired voltage and current measurements may be accessed. The time series can include measurements made by a meter, such as for power calculation and/or utility billing purposes. The paired voltage and current measurements may also be used as the input values to a calculation of impedance seen at the meter. At block 1604, a change in measured voltage divided by a change in a measured current is obtained at each of a plurality of meters associated with a transformer. At block 1606, an impedance value may be calculated. In an example, the impedance value may be based on two pair of measurements from within the time series.

Figure 17:
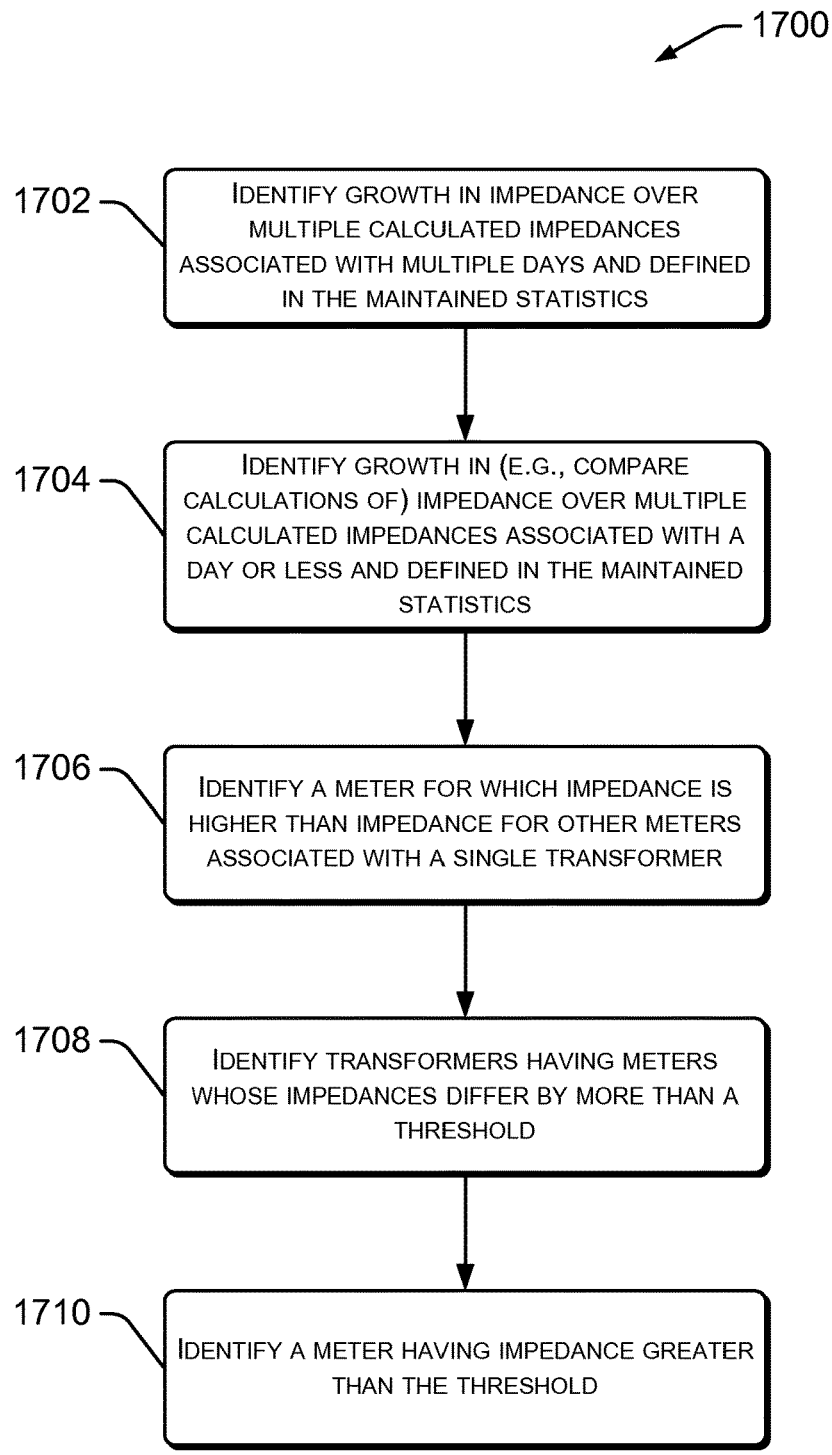
FIG. 17 is a flowchart showing several example techniques by which high impedance and/or high impedance change may be detected.

FIG. 17 shows several example techniques 1700 by which high impedance and/or high impedance change may be detected. Accordingly, optional detail associated with block 1506 in FIG. 15 is described. To detect instances of high impedance, the several example techniques shown in the several blocks of FIG. 17 may optionally be used individually or in various combinations of two of more of the techniques. At block 1702, growth in impedance is identified. The growth may be recognized as taking place over multiple calculations of impedance, which may be associated with multiple days. The multiple calculations may use input that is defined in data (e.g., paired voltage and current measurements 318 of FIG. 3). At block 1704, in a further example, the growth in impedance may be identified by comparison of multiple impedance calculations associated with a day or less. At block 1706, a high impedance condition may exist at the onset of data collection. In such an example, a meter may be identified from among several meters associated with a transformer based on an impedance that is higher than impedances associated with the other meters. At block 1708, transformers having meters whose impedances differ by more than a threshold may be flagged as a possible high impedance risk. At block 1710, a meter having impedance greater than a threshold may be identified as a possible high impedance risk.

Figure 18:
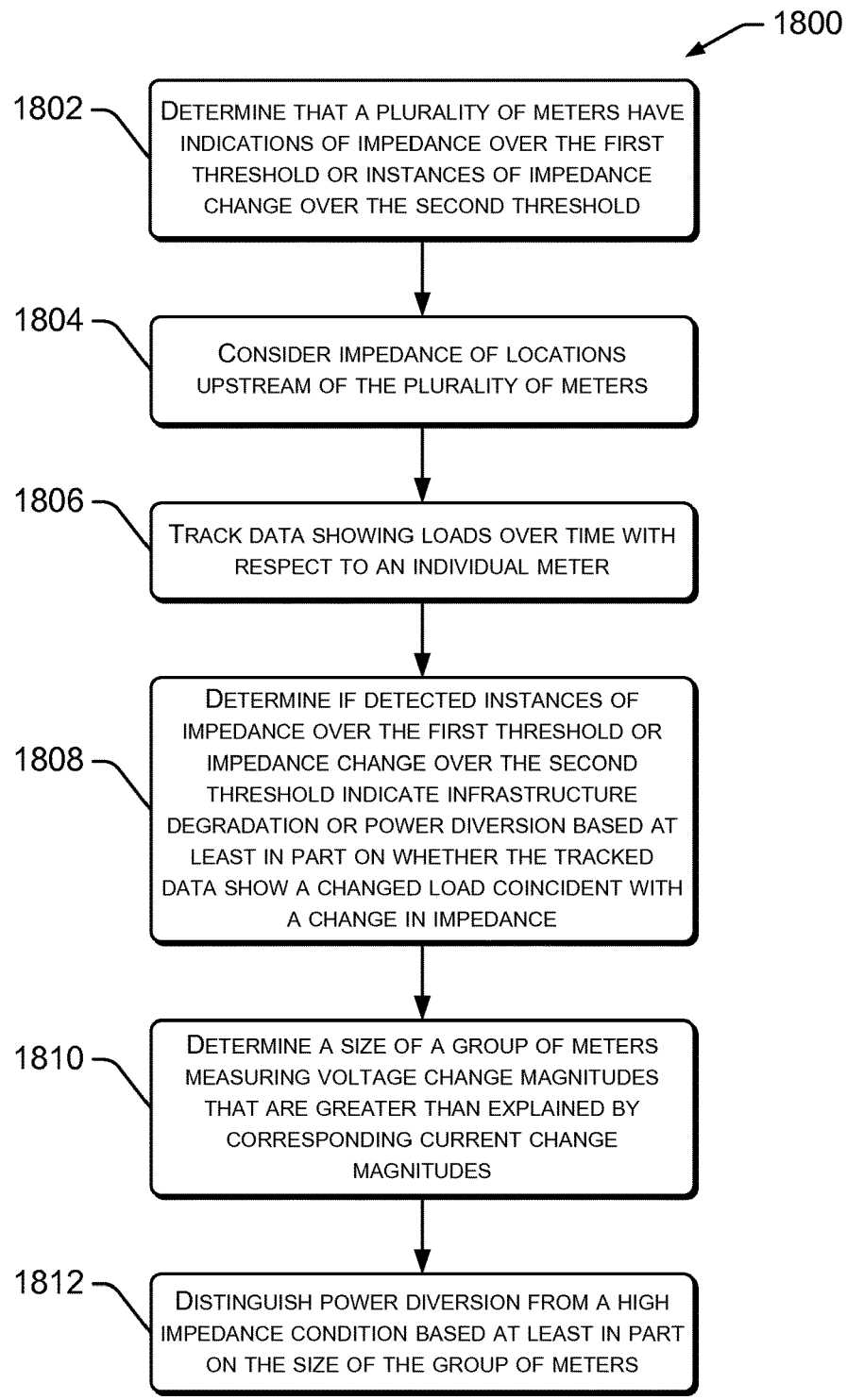
FIG. 18 is a flowchart showing several example techniques that may be used to identify and/or to flag high impedance situations.

FIG. 18 shows several example techniques 1800 that may be used to identify and/or to flag high impedance situations. The techniques may optionally be utilized in conjunction with the techniques described in FIG. 15. To identify and/or to flag high impedance situations, the several example techniques shown in the several blocks of FIG. 18 may optionally be used individually or in various combinations of two of more of the techniques.

At block 1802, it is determined whether a plurality of meters have indications of impedance over the first threshold or instances of impedance change over the second threshold. At block 1804, when multiple locations show high impedance, it may be useful to consider the impedance at locations upstream of the meters showing high impedance.

At block 1806, data showing loads over time with respect to an individual meter may be tracked. At block 1808, it may be determined whether instances of impedance at a meter over a first threshold have been detected. Alternatively or additionally, it may be determined whether impedance change at the meter over a second threshold has been detected. When impedance change is identified, it may be beneficial to distinguish impedance due to infrastructure degradation and impedance due to power diversion. In an example, these conditions may be distinguished based at least in part on whether the data tracked at block 1806 show a changed load coincident with a change in impedance. Such a coincident change would indicate power diversion; however, impedance without a coincident change in load would indicate impedance due to infrastructure degradation.

At block 1810, a size of a group of meters measuring voltage change magnitudes that are greater than explained by corresponding current change magnitudes may be determined. At block 1812, power diversion may be distinguished from a high impedance condition based at least in part on the size of the group of meters. In particular, when a larger group of meters indicates voltage change magnitudes that are greater than explained by corresponding current change magnitudes, infrastructure degradation may be indicated. In contrast, when a smaller group of meters indicates voltage change magnitudes that are greater than explained by corresponding current change magnitudes, theft may be indicated.

Figure 19:
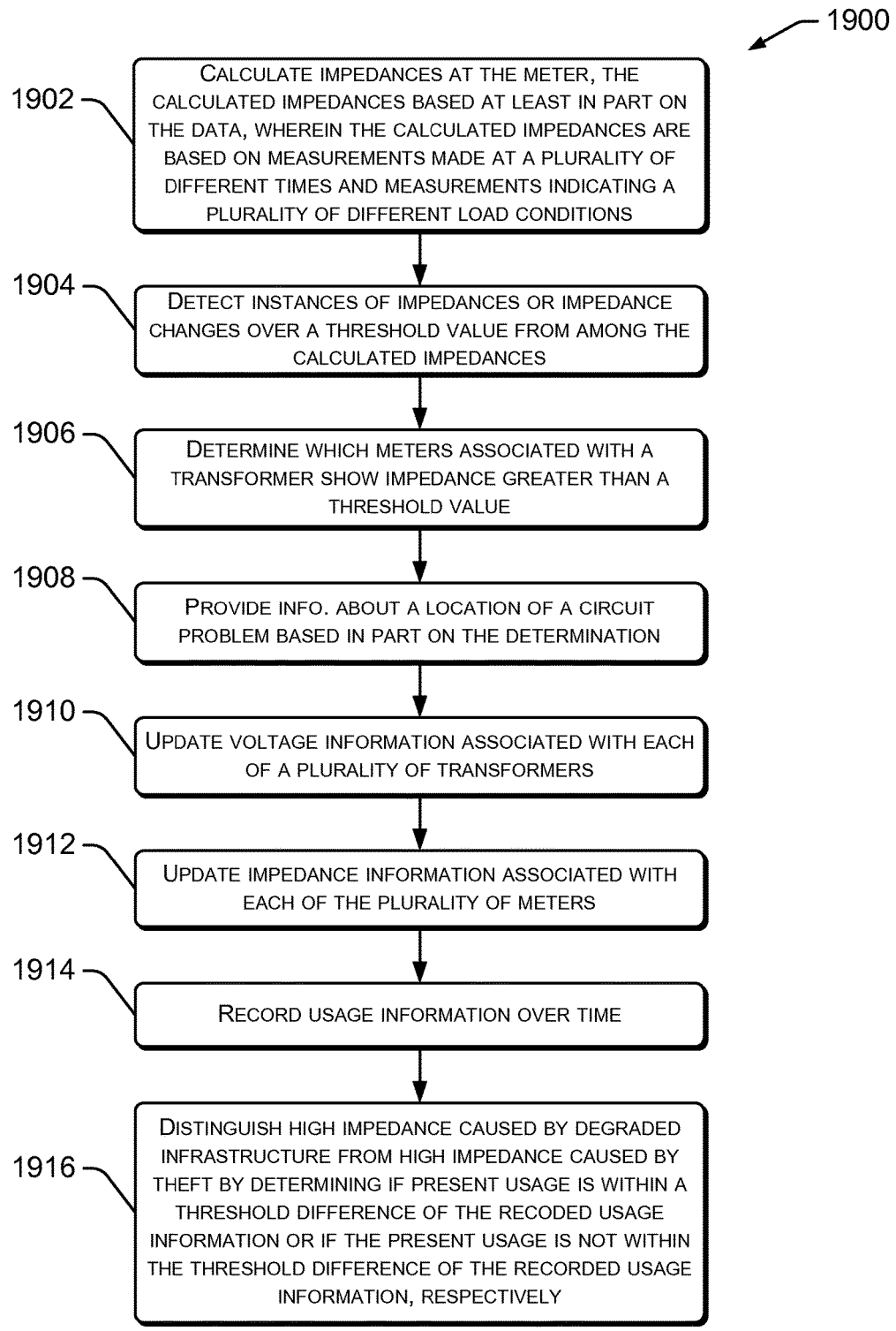
FIG. 19 is a flowchart showing several example techniques by which high impedance situations may be identified.

FIG. 19 shows several example techniques 1900 by which high impedance situations may be identified. In the course of identifying high impedance conditions, the several example techniques shown in the several blocks of FIG. 19 may optionally be used individually or in various combinations of two of more of the techniques.

At block 1902, impedances at the meter may be calculated at the meter, head office or other location. The calculated impedances may be based at least in part on voltage and current data. Such calculated impedances may be based on measurements made at a plurality of different times and measurements indicating a plurality of different load conditions. At block 1904, instances of impedance levels or impedance changes over a threshold value may be detected from among the calculated impedances.

In the example of block 1906, meters associated with a transformer determined to have impedance greater than a threshold value may be identified. At block 1908, based in part on the determination, information about a location of a circuit problem may be provided to a home office or other location.

At block 1910, voltage information associated with each of a plurality of transformers may be updated over time as additional voltage and current measurements are made, and as additional impedance calculations are made. At block 1912, impedance information associated with each of the plurality of meters may be updated. The transformer voltage information and the meter impedance information of blocks 1910 and 1912 may be provided to the home office or other location.

At block 1914, usage information over time is recoded over time, thereby recording commonly seen loads. At block 1916, high impedance caused by degraded infrastructure may be distinguished from high impedance caused by theft. In the example of block 1916, degradation and theft may be distinguished by consulting the usage information recorded over time at block 1914. In the example, a comparison is made of commonly seen loads, over time, for particular meters. If the present usage is within a threshold difference of the recoded usage information (i.e., the commonly seen loads), then infrastructure degradation should be considered. However, if the present usage is not within the threshold difference of the recorded usage information (e.g. the present usage is lower than historical), then theft should be considered.

Figure 20:
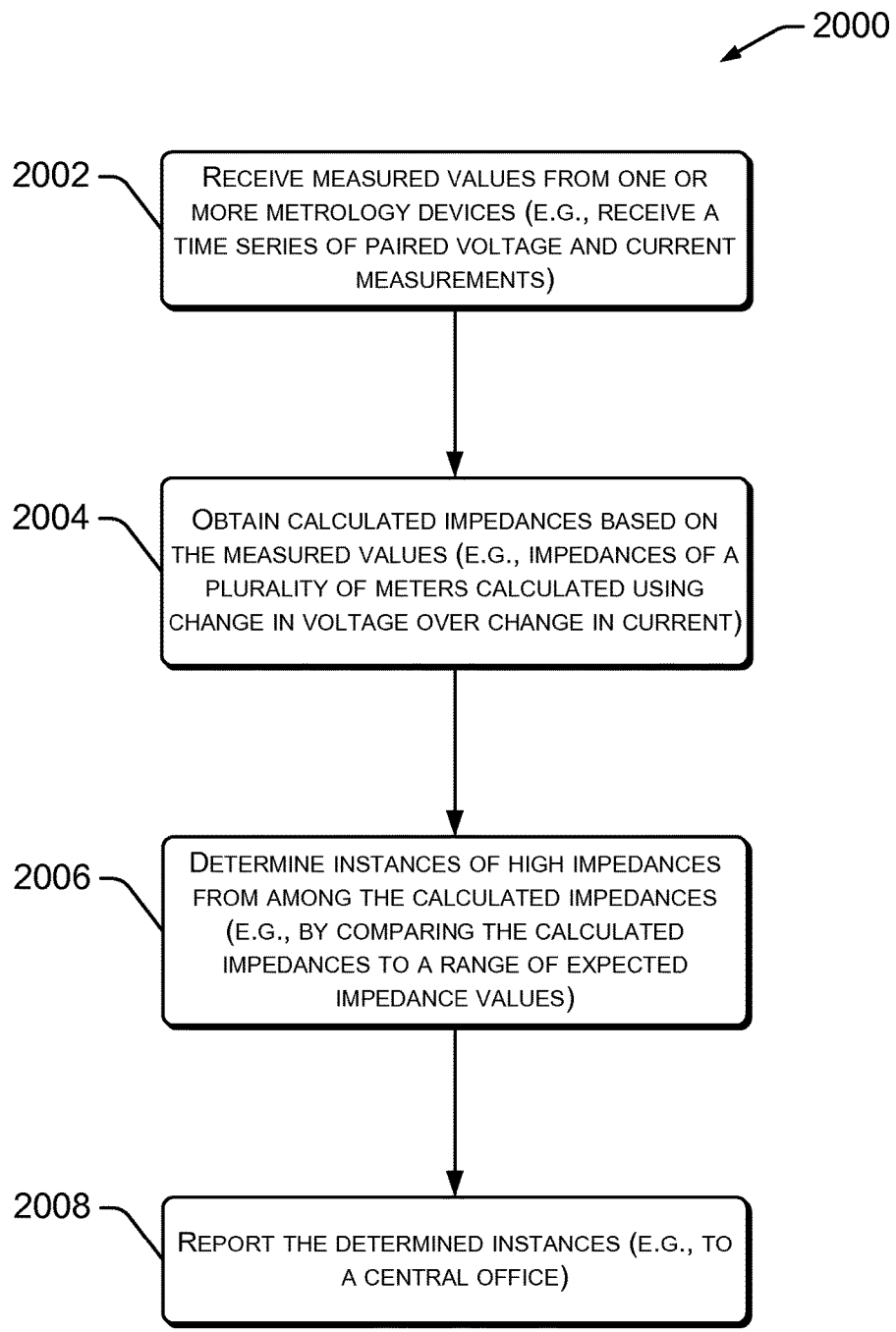
FIG. 20 is a flowchart showing an example method by which instances of high impedance wiring and/or connections may be detected.

FIG. 20 shows an example method 2000 by which instances of high impedance wiring and/or connections may be detected. At block 2002, measured values from one or more metrology devices may be received. In an example, a time series of paired voltage and current measurements is received. At block 2004, calculated impedances based on the measured values are obtained. In another example, impedances of a plurality of meters calculated using change in voltage over change in current are obtained. At block 2006, instances of high impedances from among the calculated impedances are determined. In further example, the instances of high impedances may be determined by comparing the calculated impedances to a range of expected impedance values. At block 2008, the determined instances of high impedance may be reported, such as to a central office.

CONCLUSION

Although the subject matter has been described in language specific to structural features and/or methodological acts, it is to be understood that the subject matter defined in the appended claims is not necessarily limited to the specific features or acts described. Rather, the specific features and acts are disclosed as exemplary forms of implementing the claims.

What is claimed is:

1. A method of configuring a plurality of meters that are measuring power provided by a transformer, to determine a voltage of a secondary of the transformer, wherein the transformer does not have a voltage meter, the method comprising:
   under control of one or more processors configured with executable instructions:
   making a plurality of voltage and current measurements at each of the plurality of meters associated with the transformer;
   calculating impedance values of each of the plurality of meters associated with the transformer to obtain calculated impedance values, wherein the calculated impedance values are based at least in part on measurements made at each of the plurality of meters;
   utilizing the calculated impedance values for each of the plurality of meters, and at least some of the plurality of voltage and current measurements, to calculate, for each respective meter, a transformer secondary voltage;
   averaging the calculated transformer secondary voltages of the respective meters to calculate an averaged transformer secondary voltage value;
   while power is provided to each of the plurality of meters, detecting at least one of:
      an instance of the transformer secondary voltage value, calculated by averaging voltages of the plurality of meters, below a first threshold value; or
      an instance of a change, between sequential updates of calculated transformer secondary voltage, that is greater than a second threshold value; and reporting the detected instance.

2. The method of claim 1, wherein calculating the impedance values for each of the plurality of meters comprises:
   dividing a change in measured voltage by a change in a measured current at each of the plurality of meters.

3. The method of claim 1, wherein calculating the impedance values for each of the plurality of meters comprises:
   accessing a time series of paired voltage and current measurements; and
   calculating an impedance value based on two pair of measurements from within the time series.

4. The method of claim 1, wherein calculating impedance values for each of the plurality of meters associated with the transformer comprises:
   identifying growth in impedance in one or more of the plurality of meters over multiple calculated impedances associated with multiple days;
   identifying growth in impedance in one or more of the plurality of meters over multiple calculated impedances associated with a day or less;
   identifying a meter for which impedance is higher than impedance for other meters associated with the transformer; and
   identifying a meter having impedance greater than the first threshold value.

5. The method of claim 1, additionally comprising:
   identifying meters that have impedance values over the first threshold value or instances of impedance change over the second threshold value;
   locating at least one upstream meter of one or more of the identified meters; and
   calculating the impedance of the at least one upstream meter.

6. The method of claim 1, additionally comprising:
   tracking data showing loads over time with respect to an individual meter; and
   determining if calculated impedance over a third threshold value or impedance change over a fourth threshold value indicate power provided through degraded infrastructure or power diversion within an electrical grid based at least in part on the data showing loads over time.

7. The method of claim 1, additionally comprising:
   determining a size of a group of meters measuring voltage change magnitudes that are greater than explained by corresponding current change magnitudes; and
   distinguishing power diversion from a high impedance condition based at least in part on the size of the group of meters.

8. A circuit card adapted for use in a meter, the circuit card comprising:
   a processor;
   memory in communication with the processor;
   data, based on voltage and current measurements, maintained in the memory; and
   an analytics application, operable by the processor and defined at least in part in the memory, to input the data and to perform actions comprising:
      calculating impedance values at the meter to obtain calculated impedance values, wherein the calculated impedance values are based at least in part on the data, and wherein the calculated impedance values are based on measurements made at a plurality of different times and measurements indicating a plurality of different load conditions, wherein the calculated impedance values are based at least in part on measurements made at the meter;
      utilizing at least some of the calculated impedance values to calculate a secondary voltage value of a transformer to which the meter is connected; and
      while power is provided to the meter, detecting at least one of:
         instances of the secondary voltage values of the transformer below a first threshold value; or
         instances of change between sequential updates of calculated transformer secondary voltage values is greater than a second threshold value; and
      reporting the detected instances.

9. The circuit card of claim 8, wherein actions of the circuit card additionally comprise:

comparing the calculated secondary voltage value of the transformer to a threshold of permitted voltage variability; and responsive to the calculated secondary voltage value exceeding the threshold of permitted voltage variability, flagging the transformer for possible electrical diversion.

10. The circuit card of claim 8, wherein actions of the circuit card additionally comprise:

comparing the calculated secondary voltage value of the transformer to predicted voltage based at least in part on voltage falloff of transformers based on distance from a substation; and responsive to the calculated secondary voltage value being less that predicted voltage, flagging possible unauthorized transformer or unauthorized load.

11. A system, comprising the circuit card of claim 8, and a central office computing device, wherein the system is configured for acts comprising:

comparing secondary voltages of transformers on a same feeder line;

establishing a ranking of transformers based on secondary voltage;

detecting a change in the ranking; and reporting the detected change in the ranking.

12. A system, comprising the circuit card of claim 8, wherein the system is configured for acts comprising:

comparing secondary voltages of transformers on a same feeder line; and providing information about a location of an unauthorized transformer based at least in part on the comparison.

13. A system, comprising the circuit card of claim 8, wherein the system is configured for acts comprising:

determining if transformer load change was contemporaneous with a change in secondary voltage ranking of a plurality of transformers; and responsive to failure of transformer load change to explain the change in secondary voltage ranking of the plurality of transformers, reporting possible theft.

14. A system, comprising the circuit card of claim 8, wherein the system is configured for acts comprising:

identify a voltage drop at the transformer that is not correlated to current use measured by meters connected to the transformer; and report a likelihood of power diversion located at the transformer.

15. A system, comprising the circuit card of claim 8, wherein the system additionally comprises:

one or more data concentrator devices, to process instances of secondary voltage values and/or the instances of change between sequential updates of calculated transformer secondary voltage values.

16. One or more non-transitory computer-readable media storing computer-executable instructions that, when executed, cause one or more processors to perform acts comprising:

receiving a plurality of measured voltage and current values from a plurality of metrology devices of a plurality of meters, respectively;

calculating impedance values of each of the plurality of meters based on the plurality of measured voltage and current values to obtain calculated impedance values, wherein the calculated impedance values are based at least in part on measurements made at the plurality of meters;

utilizing the calculated impedance values for each of the plurality of meters, and at least some of the plurality of measured voltage and current values, to calculate, for each respective meter, a transformer secondary voltage value of a transformer;

averaging the calculated transformer secondary voltage values of the respective meters to calculate an averaged transformer secondary voltage value; and while power is provided to the plurality of meters, detecting at least one of:

instances of the averaged transformer secondary voltage values below a first threshold value; or instances of a change between sequential updates of calculated transformer secondary voltage values is greater than a second threshold value; and reporting the detected instances.

17. One or more non-transitory computer-readable media as recited in claim 16, wherein the acts additionally comprise:

identifying if a level of variability of the averaged transformer secondary voltage value is more than a threshold; and responsive to exceeding the threshold, flagging the transformer for investigation.

18. One or more non-transitory computer-readable media as recited in claim 16, wherein determining instances of high impedances comprises:

determining which of the plurality of meters are experiencing impedance over a threshold and which are not experiencing impedance over the threshold.

19. One or more non-transitory computer-readable media as recited in claim 16, wherein the acts additionally comprise:

distinguishing meters having high impedance due to degraded infrastructure from meters having high impedance due to diversion of electricity, wherein the distinguishing is based at least in part on at least one of:

a size of a group of meters for which a change in voltage is greater than an expected threshold value based on a magnitude of a change in current; and a comparison of commonly seen loads, over time, for particular meters.

20. One or more non-transitory computer-readable media as recited in claim 16, wherein at least some of the acts are performed by operation of processors on:

a plurality of meters;

a back office server;

a circuit card in a meter;

a concentrator; or a router.

21. One or more non-transitory computer-readable media as recited in claim 16, wherein the acts are performed in part by operation of processors on each of the plurality of meters, and additionally comprise:

receiving a time series of paired voltage and current measurements; and calculating impedance based on sequential pairs of voltage and current measurements.

* * * * *